United States Patent
Hsu et al.

(10) Patent No.: US 7,829,330 B2
(45) Date of Patent: Nov. 9, 2010

(54) STRESSCOPINS AND THEIR USES

(75) Inventors: Sheau Yu Hsu, Menlo Park, CA (US); Aaron J. W. Hsueh, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/935,350

(22) Filed: Nov. 5, 2007

(65) Prior Publication Data

US 2008/0145927 A1 Jun. 19, 2008

Related U.S. Application Data

(62) Division of application No. 10/682,794, filed on Oct. 8, 2003, now Pat. No. 7,291,341, which is a division of application No. 09/682,706, filed on Oct. 9, 2001, now abandoned.

(60) Provisional application No. 60/244,128, filed on Oct. 26, 2000, provisional application No. 60/276,615, filed on Mar. 15, 2001.

(51) Int. Cl.
*C12N 15/00* (2006.01)
*C12N 15/63* (2006.01)

(52) U.S. Cl. .................... 435/320.1; 435/325

(58) Field of Classification Search ............... 435/320.1
See application file for complete search history.

(56) References Cited

U.S. PATENT DOCUMENTS

| 2003/0036507 A1 | 2/2003 | Vale et al. |
| 2004/0143095 A1 | 7/2004 | Vale et al. |

FOREIGN PATENT DOCUMENTS

| WO | WO 9700063 | * | 1/1997 |
| WO | WO0212307 A1 | | 2/2002 |

OTHER PUBLICATIONS

Wolf et al, (Mol Biol Med, 5(1): 1-2,1999).*
Horlick et al, (Protein Expression and Purification, 9, 301-308, 1997).*
Bale et al., "Mice deficient for corticotropin-releasing hormone receptor-2 display anxiety-like behaviour and are hypersensitive to stress," Nat. Genet., 2000, 24(4):410-414.
Chen et al., "Expression cloning of a human corticotropin-releasing-factor receptor," Proc. Natl. Acad. Sci. USA, 1993, 90(19):8967-8971.
Coste et al., "Abnormal adaptations to stress and impaired cardiovascular function in mice lacking corticotropin-releasing hormone receptor-2," Nat. Genet., 2000, 24(4):403-409.
Donaldson et al., "Cloning and Characterization of Human Urocortin," Endocrinology, 1996, 137(5):2167-2170.
Grammatopoulos et al., "A Novel Spliced Variant of the Type 1 Corticotropin-Releasing Hormone Receptor with a Deletion in the Seventh Transmembrane Domain Present in the Human Pregnant Term Myometrium and Fetal Membranes," Mol. Endocrinol., 1999, 13(12):2189-2202.
Hsu et al., "Human stresscopin and stresscopin-related peptide are selective ligands for the type 2 corticotropin-releasing hormone receptor," Nat. Med., 2001, 7(5):605-611.
Lewis et al., "Identification of urocortin III, an additional member of the corticotropin-releasing factor (CRF) family with high affinity for the CRF2 receptor," Proc. Natl. Acad. Sci. U.S.A., 2001, 98(13):7570-7575.
Liaw et al., "Cloning and characterization of the human corticotropin-releasing factor-2 receptor complementary deoxyribonucleic acid," Endocrinology, 1996, 137(1):72-77.
Reyes et al., "Urocortin II: A Member of the Corticotropin-Releasing Factor (CRF) Neuropeptide Family that is Selectively Bound By Type 2 CRF Receptors," Proc. Natl. Acad. Sci. USA, 2001, 98(5):2843-2848.
Shibahara et al., "Isolation and sequence analysis of the human corticotropin-releasing factor precurser gene," EMBO J, 1983, 2(5):775-779.
Smith et al., "Corticotropin Releasing Factor Receptor 1-Deficient Mice Display Decreased Anxiety, Impaired Stress Response, and Aberrant Neuroendocrine Development," Neuron, 1998, 20(6):1093-1102.

* cited by examiner

*Primary Examiner*—Anne-Marie Falk
*Assistant Examiner*—Magdalene K Sgagias
(74) *Attorney, Agent, or Firm*—Bozicevic, Field & Francis LLP; Pamela J. Sherwood

(57) ABSTRACT

The invention provides novel nucleic acids and polypeptides, referred to herein as stresscopin 1 and stresscopin 2, which preferentially activate the CRH-R2 receptor over the R1 receptor. Stresscopins, analogs and mimetics, and related CRH-R2 agonists suppress food intake and heat-induced edema; but do not induce substantial release of ACTH. Stresscopin also finds use in the recovery phase of stress responses, as an anti-inflammatory agent, as a hypotensive agent, as a cardioprotective agent, and in the treatment of psychiatric and anxiolytic disorders. Stresscopin nucleic acid compositions find use in identifying homologous or related proteins and the DNA sequences encoding such proteins; in producing compositions that modulate the expression or function of the protein; and in studying associated physiological pathways.

8 Claims, 8 Drawing Sheets

FIG. 1A

Stresscopin 1

| | |
|---|---|
| ATGACCAGGTGTGCTCTGCTGTTGCTGATGGTCCTGATGTTGGGCAGAGTC | 51 |
|   M  T  R  C  A  L  L  L  M  V  L  M  L  G  R  V | |
| CTGGTTGTCCCAGTGACCCCTATCCCAACCTTCCAGCTCCGCCCTCAGAAT | 102 |
|   L  V  V  P  V  T  P  I  P  T  F  Q  L  R  P  Q  N | |
| TCTCCCCAGACCACTCCCCGACCTGCGGCCTCAGAGAGCCCCTCAGCTGCT | 153 |
|   S  P  Q  T  T  P  R  P  A  A  S  E  S  P  S  A  A | |
| CCCACATGGCCGTGGGCTGCCCAGAGCCACTGCAGCCCCACCCGCCACCCT | 204 |
|   P  T  W  P  A  A  Q  S  H  C  S  P  T  R  H  P | |
| GGCTCGCGCATTGTCCTATCGCTGGATGTCCCCATCGGCCTCTTGCAGATC | 255 |
|   G  S  R  I  V  L  S  L  D  V  P  I  G  L  L  Q  I | |
| TTACTGGAGCAAGCCCGGGCCAGGGCTGCCAGGGAGCAGGCCACCACCAAC | 306 |
|   L  L  E  Q  A  R  A  R  A  A  R  E  Q  A  T  T  N | |
| GCCCGCATCCTGGCCCGTGTCGGCCACTGCTGA | 339 |
|   A  R  I  L  A  R  V  G  H  C  * | |

FIG. 1B

Stresscopin 2

| | |
|---|---|
| ATGCTGATGCCGGTCCACTTCCTGCTGCTCCTGCTGCTGCTCCTGGGGGGC | 51 |
|   M  L  M  P  V  H  F  L  L  L  L  L  L  L  G  G | |
| CCCAGGACAGGCCTCCCCCACAAGTTCTACAAAGCCAAGCCCATCTTCAGC | 102 |
|   P  R  T  G  L  P  H  K  F  Y  K  A  K  P  I  F  S | |
| TGCCTCAACACCGCCCTGTCTGAGGCTGAGAAGGGCCAGTGGGAGGATGCA | 153 |
|   C  L  N  T  A  L  S  E  A  E  K  G  Q  W  E  D  A | |
| TCCCTGCTGAGCAAGAGGAGCTTCCACTACCTGCGCAGCAGAGACGCCTCT | 204 |
|   S  L  L  S  K  R  S  F  H  Y  L  R  S  R  D  A  S | |
| TCGGGAGAGGAGGAGGAGGGCAAAGAGAAAAAGACTTTCCCCATCTCTGGG | 255 |
|   S  G  E  E  E  G  K  E  K  K  T  F  P  I  S  G | |
| GCCAGGGGTGGAGCCGGAGGCACCCGTTACAGATACGTGTCCCAAGCACAG | 306 |
|   A  R  G  G  A  G  G  T  R  Y  R  Y  V  S  Q  A  Q | |
| CCCAGGGGAAAGCCACGCCAGGACACAGCCAAGAGTCCCCACCGCACCAAG | 357 |
|   P  R  G  K  P  R  Q  D  T  A  K  S  P  H  R  T  K | |
| TTCACCCTGTCCCTCGACGTCCCCACCAACATCATGAACCTCCTCTTCAAC | 408 |
|   F  T  L  S  L  D  V  P  T  N  I  M  N  L  L  F  N | |
| ATCGCCAAGGCCAAGAACCTGCGTGCCCAGGCGGCCGCCAATGCCCACCTG | 459 |
|   I  A  K  A  K  N  L  R  A  Q  A  A  A  N  A  H  L | |
| ATGGCGCAAATTGGGAGGAAGAAGTAG | 486 |
|   M  A  Q  I  G  R  K  K  * | |

FIG. 1C

```
hCRH          153  RSEEPPISLDLTFHLLREVLEMARAEQLAQQAHSNRKLMEII
hCRH          144  RSEEPPISLDLTFHLLREVLEMARAEQLAQQAHSNRIIFDSV
hUrocortin     81  RRDNPSLSIDLTFHLLRTLLELARTQSQRERAEQNRIIFDSV
hUrocortin     79  RRDDPPLSIDLTFHLLRTLLELARTQSQRERAEQNRIIFDSV
gUrotensin I  102  RNDDPPISIDLTFHLLRNMIEMARNENQREQAGLNRKYLDEV
sCRH1         119  RSEEPPISLDLTFHLLREVLEMARAEQLAQQAHSNRKMMEIF
sCRH2         119  RSEEPPISLDLTFHLLREVLEMARAEQLVQQAHSNRKMMEIF
fSauvagine         QGPPISIDLSLELLRKMIEIEKQEKEKQQAANNRLLLDTI hStresscopin1  67  HPGSRIVLSLDVPIGLLQILLEQARARAAREQATTNARILARV
hStresscopin2 118       TKFTLSLDVPTNIMNLLFNIAKAKNLRAQAAANAHLMAQI
pStresscopin  108       SRLTLSLDVPTNIMNVLFDVAKAKNLRAKAAENARLLAHI
```

FIG. 1D

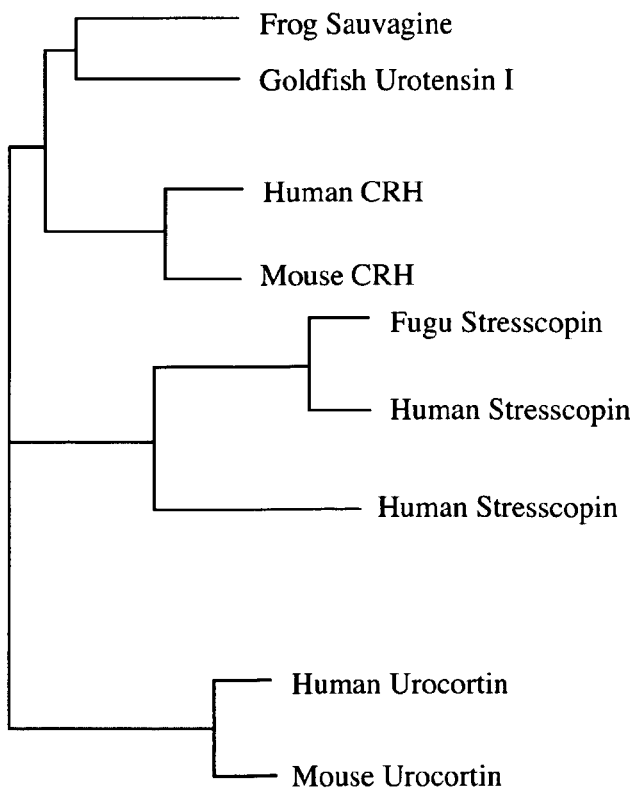

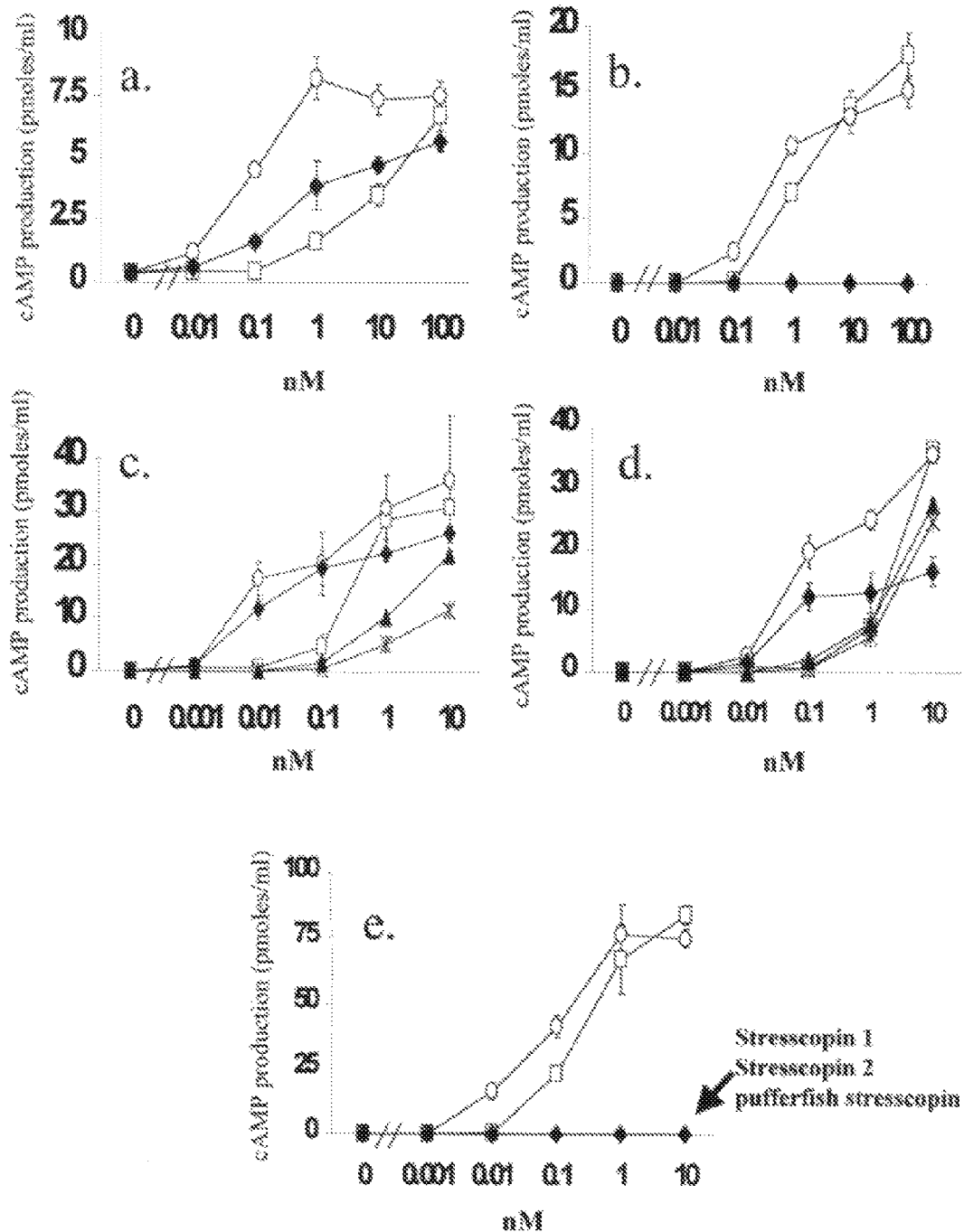
FIG. 3A-E

SEQUENCE LISTING

<160> NUMBER OF SEQ ID NOS: 15

<210> SEQ ID NO 1
<211> LENGTH: 339
<212> TYPE: DNA
<213> ORGANISM: Homo Sapiens

<400> SEQUENCE: 1

```
atgaccaggt gtgctctgct gttgctgatg gtcctgatgt tgggcagagt cctggttgtc      60
ccagtgaccc ctatcccaac cttccagctc cgccctcaga attctcccca gaccactccc     120
cgacctgcgg cctcagagag cccctcagct gctcccacat ggccgtgggc tgcccagagc     180
cactgcagcc ccacccgcca ccctggctcg cgcattgtcc tatcgctgga tgtccccatc     240
ggcctcttgc agatcttact ggagcaagcc cgggccaggg ctgccaggga gcaggccacc     300
accaacgccc gcatcctggc ccgtgtcggc cactgctga                            339
```

<210> SEQ ID NO 2
<211> LENGTH: 112
<212> TYPE: PRT
<213> ORGANISM: Homo Sapiens

<400> SEQUENCE: 2

```
Met Thr Arg Cys Ala Leu Leu Leu Leu Met Val Leu Met Leu Gly Arg
 1               5                  10                  15
```

Val Leu Val Val Pro Val Thr Pro Ile Pro Thr Phe Gln Leu Arg Pro
            20                  25                  30

Gln Asn Ser Pro Gln Thr Thr Pro Arg Pro Ala Ala Ser Glu Ser Pro
        35                  40                  45

Ser Ala Ala Pro Thr Trp Pro Trp Ala Ala Gln Ser His Cys Ser Pro
    50                  55                  60

Thr Arg His Pro Gly Ser Arg Ile Val Leu Ser Leu Asp Val Pro Ile
65                  70                  75                  80

Gly Leu Leu Gln Ile Leu Leu Glu Gln Ala Arg Ala Arg Ala Ala Arg
                85                  90                  95

Glu Gln Ala Thr Thr Asn Ala Arg Ile Leu Ala Arg Val Gly His Cys
            100                 105                 110

<210> SEQ ID NO 3
<211> LENGTH: 43
<212> TYPE: PRT
<213> ORGANISM: Homo sapiens

<400> SEQUENCE: 3

His Pro Gly Ser Arg Ile Val Leu Ser Leu Asp Val Ile Leu Gly Leu
1               5                   10                  15

Leu Gln Ile Leu Leu Glu Gln Ala Arg Ala Arg Ala Ala Arg Glu Gln
            20                  25                  30

Ala Thr Thr Asn Ala Arg Ile Leu Ala Arg Val
        35                  40

<210> SEQ ID NO 4
<211> LENGTH: 486
<212> TYPE: DNA
<213> ORGANISM: Homo sapiens

<400> SEQUENCE: 4

| | | |
|---|---|---|
| atg ctg atg ccg gtc cac ttc ctg ctg ctc ctg ctg ctc ctg ggg | | 48 |
| ggc ccc agg aca ggc ctc ccc cac aag ttc tac aaa gcc aag ccc atc | | 96 |
| ttc agc tgc ctc aac acc gcc ctg tct gag gct gag aag ggc cag tgg | | 144 |
| gag gat gca tcc ctg ctg agc aag agg agc ttc cac tac ctg cgc agc | | 192 |
| aga gac gcc tct tcg gga gag gag gag gag ggc aaa gag aaa aag act | | 240 |
| ttc ccc atc tct ggg gcc agg ggt gga gcc gga ggc acc cgt tac aga | | 288 |
| tac gtg tcc caa gca cag ccc agg gga aag cca cgc cag gac aca gcc | | 336 |
| aag agt ccc cac cgc acc aag ttc acc ctg tcc ctc gac gtc ccc acc | | 384 |
| aac atc atg aac ctc ctc ttc aac atc gcc aag gcc aag aac ctg cgt | | 432 |
| gcc cag gcg gcc gcc aat gcc cac ctg atg gcg caa att ggg agg aag | | 480 |
| aag tag | | 486 |

<210> SEQ ID NO 5
<211> LENGTH: 161
<212> TYPE: PRT
<213> ORGANISM: Homo sapiens

<400> SEQUENCE: 5

Met Leu Met Pro Val His Phe Leu Leu Leu Leu Leu Leu Leu Leu Gly
1               5                   10                  15

Gly Pro Arg Thr Gly Leu Pro His Lys Phe Tyr Lys Ala Lys Pro Ile
            20                  25                  30

```
Phe Ser Cys Leu Asn Thr Ala Leu Ser Glu Ala Glu Lys Gly Gln Trp
             35                  40                  45

Glu Asp Ala Ser Leu Leu Ser Lys Arg Ser Phe His Tyr Leu Arg Ser
 50                  55                  60

Arg Asp Ala Ser Ser Gly Glu Glu Glu Gly Lys Glu Lys Lys Thr
 65                  70                  75                  80

Phe Pro Ile Ser Gly Ala Arg Gly Gly Ala Gly Gly Thr Arg Tyr Arg
                     85                  90                  95

Tyr Val Ser Gln Ala Gln Pro Arg Gly Lys Pro Arg Gln Asp Thr Ala
                    100                 105                 110

Lys Ser Pro His Arg Thr Lys Phe Thr Leu Ser Leu Asp Val Pro Thr
                115                 120                 125

Asn Ile Met Asn Leu Leu Phe Asn Ile Ala Lys Ala Lys Asn Leu Arg
            130                 135                 140

Ala Gln Ala Ala Ala Asn Ala His Leu Met Ala Gln Ile Gly Arg Lys
145                 150                 155                 160

Lys

<210> SEQ ID NO 6
<211> LENGTH: 40
<212> TYPE: PRT
<213> ORGANISM: Homo sapiens

<400> SEQUENCE: 6

Thr Lys Phe Thr Leu Ser Leu Asp Val Pro Thr Asn Ile Met Asn Leu
 1               5                  10                  15

Leu Phe Asn Ile Ala Lys Ala Lys Asn Leu Arg Ala Gln Ala Ala Ala
                20                  25                  30

Asn Ala His Leu Met Ala Gln Ile
            35                  40

<210> SEQ ID NO 7
<211> LENGTH: 42
<212> TYPE: PRT
<213> ORGANISM: Homo sapiens

<400> SEQUENCE: 7

Arg Ser Glu Glu Pro Pro Ile Ser Leu Asp Leu Thr Phe His Leu Leu
 1               5                  10                  15

Arg Glu Val Leu Glu Met Ala Arg Ala Glu Gln Leu Ala Gln Gln Ala
                20                  25                  30

His Ser Asn Arg Lys Leu Met Glu Ile Ile
            35                  40

<210> SEQ ID NO 8
<211> LENGTH: 42
<212> TYPE: PRT
<213> ORGANISM: Mus musculus

<400> SEQUENCE: 8

Arg Ser Glu Glu Pro Pro Ile Ser Leu Asp Leu Thr Phe His Leu Leu
 1               5                  10                  15

Arg Glu Val Leu Glu Met Ala Arg Ala Glu Gln Leu Ala Gln Gln Ala
                20                  25                  30

His Ser Asn Arg Ile Ile Phe Asp Ser Val
            35                  40
```

<210> SEQ ID NO 9
<211> LENGTH: 42
<212> TYPE: PRT
<213> ORGANISM: Homo sapiens

<400> SEQUENCE: 9

Arg Arg Asp Asn Pro Ser Leu Ser Ile Asp Leu Thr Phe His Leu Leu
1               5                   10                  15

Arg Thr Leu Leu Glu Leu Ala Arg Thr Gln Ser Gln Arg Glu Arg Ala
            20                  25                  30

Glu Gln Asn Arg Ile Ile Phe Asp Ser Val
        35                  40

<210> SEQ ID NO 10
<211> LENGTH: 42
<212> TYPE: PRT
<213> ORGANISM: Mus musculus

<400> SEQUENCE: 10

Arg Arg Asp Asp Pro Pro Leu Ser Ile Asp Leu Thr Phe His Leu Leu
1               5                   10                  15

Arg Thr Leu Leu Glu Leu Ala Arg Thr Gln Ser Gln Arg Glu Arg Ala
            20                  25                  30

Glu Gln Asn Arg Ile Ile Phe Asp Ser Val
        35                  40

<210> SEQ ID NO 11
<211> LENGTH: 42
<212> TYPE: PRT
<213> ORGANISM: Carassius auratus

<400> SEQUENCE: 11

Arg Asn Asp Asp Pro Pro Ile Ser Ile Asp Leu Thr Phe His Leu Leu
1               5                   10                  15

Arg Asn Met Ile Glu Met Ala Arg Asn Glu Asn Gln Arg Glu Gln Ala
            20                  25                  30

Gly Leu Asn Arg Lys Tyr Leu Asp Glu Val
        35                  40

<210> SEQ ID NO 12
<211> LENGTH: 42
<212> TYPE: PRT
<213> ORGANISM: Catostomus commersoni

<400> SEQUENCE: 12

Arg Ser Glu Glu Pro Pro Ile Ser Leu Asp Leu Thr Phe His Leu Leu
1               5                   10                  15

Arg Glu Val Leu Glu Met Ala Arg Ala Glu Gln Leu Ala Gln Gln Ala
            20                  25                  30

His Ser Asn Arg Lys Met Met Glu Ile Phe
        35                  40

<210> SEQ ID NO 13
<211> LENGTH: 42
<212> TYPE: PRT
<213> ORGANISM: Catostomus commersoni

<400> SEQUENCE: 13

Arg Ser Glu Glu Pro Pro Ile Ser Leu Asp Leu Thr Phe His Leu Leu
1               5                   10                  15

Arg Glu Val Leu Glu Met Ala Arg Ala Glu Gln Leu Val Gln Gln Ala

-continued

```
                    20                  25                  30
His Ser Asn Arg Lys Met Met Glu Ile Phe
        35                  40

<210> SEQ ID NO 14
<211> LENGTH: 40
<212> TYPE: PRT
<213> ORGANISM: Phyllomedusa sauvagei

<400> SEQUENCE: 14

Gln Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 15
<211> LENGTH: 40
<212> TYPE: PRT
<213> ORGANISM: Takifugu rubripes

<400> SEQUENCE: 15

Ser Arg Leu Thr Leu Ser Leu Asp Val Pro Thr Asn Ile Met Asn Val
1               5                   10                  15

Leu Phe Asp Val Ala Lys Ala Lys Asn Leu Arg Ala Lys Ala Ala Glu
            20                  25                  30

Asn Ala Arg Leu Leu Ala His Ile
        35                  40
```

STRESSCOPINS AND THEIR USES

INTRODUCTION

Mammals respond to stress through interlinked endocrine, neuroendocrine, autonomic and behavioral pathways. Activation of the autonomic nervous system elicits the release of catecholamines, whereas hypothalamic secretion of corticotropin releasing hormone (CRH) leads to pituitary secretion of adrenocorticotrophic hormone (ACTH), which, in turn, stimulates glucocorticoid secretion by the adrenal cortex. These stress-responses can provide a vital short-term metabolic lift, but when triggered inappropriately can also cause severe diseases. For example, anxiety and depression affect over 100 million patients worldwide every year, and depression is the leading cause of suicide, which claims thousands of lives each year in the U.S. Anxiety is among the most commonly observed group of CNS disorders, which includes phobias or irrational fears, panic attacks, obsessive-compulsive disorders and other fear and tension syndromes. Another potentially deleterious response to stress is hypertension, which can lead to fatal heart disease and stroke.

The physiological response to stress is integrated through corticotropin releasing hormone (CRH), and related factors (Shibahara et al (1983) *EMBO J.* 2 (5):775-779). CRH is a 41-amino acid peptide synthesized in the hypothalamus. It is a ligand for two receptors, CRH-R1 and CRH-R2. Another known ligand for the CRH receptors is urocortin, which is a 40 amino acid peptide having substantial sequence similarity with the fish protein urotensin and to CRH (Donaldson et al. (1996) *Endocrinology* 137 (5):2167-2170). These receptors have a seven-transmembrane structure, and belong to the family of G-protein coupled receptors, whose actions are mediated through activation of adenylate cyclase. The type-1 receptor is expressed in many areas of the brain, as well as in the pituitary, gonads, and skin (Chen et al. (1993) *P.N.A.S.* 90:8967-8971). The type-2 receptor is expressed in the brain, cardiac and skeletal muscle, epididymis, and the gastrointestinal tract (Liaw et al. (1996) *Endocrinology* 137 (1):72-77). In addition, there is a CRH-R2 splice isoform found in human brain (Grammatopoulos et al. (1999) *Mol. Endocrinol.* 13 (12):2189-2202).

Although the two receptors share 70% sequence identity, they differ in their ligand binding affinity. CRH itself has a much higher affinity for CRH-R1, while urocortin is equally effective at binding both the R1 and the R2 receptors. It is also believed that the receptors differ in their physiological role. An inverse relationship between the CRH-R1 and CRH-R2 receptor systems have been reported in an anxiety model, suggesting that CRH neuronal systems may be comprised of two separate, but interrelated, subdivisions that can be coordinately and inversely regulated by stress, anxiety, or anxiolytic drugs.

Mice lacking CRH-R1 display markedly reduced anxiety, and fail to exhibit the normal hormonal response to stress (Smith et al, (1998) *Neuron* 20:1093-1102). Animals having a targeted disruption in CRH-R2 have normal initiation of stress responses, but have deficiencies in the maintenance and recovery phases. For example, stress coping behaviors associated with de-arousal were reduced in these knock-out mice. The mice were also hypersensitive to stress, and displayed increased anxiety-like behavior (Bale et al. (2000) *Nat. Genet.* 24:410-414). CRH-R2 may also mediate peripheral human dynamic effects, including enhanced cardiac performance and reduced blood pressure, as well as cardiovascular homeostasis (Coste et al. (2000) *Nat. Genet.* 24:403-409). CRH-R2 signaling is essential for coping with the hypertension initiated during stress. Mutant mice have normal basal feeding and weight gain, but decreased food intake following food deprivation, suggesting a role of CRH-R2 in feeding behavior and reduced gastric emptying. In addition, CRH-R2 signaling may be involved in the suppression of immune responses associated with stress.

There is considerable interest for clinical and research purposes in the discovery and development of agents that act on these receptors, particularly where there can be enhanced specificity of action over existing ligands.

SUMMARY OF THE INVENTION

Stresscopin nucleic acid compositions and their encoded polypeptides and variants thereof are provided. Stresscopins are novel and selective ligands for the CRH-R2 receptor, and thus find use where it is desirable to specifically induce the CRH-R2 and not the CRH-R1 response pathway. In addition to use as a therapeutic agent, stresscopins are utilized in screening and research methods for the determination of specific analogs, agonists, antagonists and mimetics.

Stresscopins, analogs and mimetics, and related CRH-R2 agonists suppress food intake and heat-induced edema, but unlike CRH and urocortin, stresscopins do not induce substantial release of pituitary ACTH and adrenal glucocorticoids. Stresscopins also find use in the recovery phase of stress responses, as an anti-inflammatory agent, as a hypotensive agent, as a cardioprotective agent, and in the treatment of psychiatric and anxiolytic disorders.

The invention also provides diagnostics and therapeutics comprising stresscopin nucleic acids, their corresponding genes and gene products, antisense nucleotides, and antibodies specific for one or more epitopes of the stresscopin polypeptide. The nucleic acid compositions find use in identifying homologous or related genes; for production of the encoded protein; in producing compositions that modulate the expression or function of its encoded protein; for gene therapy; mapping functional regions of the protein; and in studying associated physiological pathways. In addition, modulation of the gene activity in vivo is used for prophylactic and therapeutic purposes.

BRIEF DESCRIPTION OF THE DRAWINGS

FIG. 1A. Nucleic acid sequence and amino acid sequence of stresscopin 1 (SEQ ID NOS:1-2). The pre-pro region of stresscopin 1 polypeptide is 46 amino acids and is lightly shaded, while the putative mature stresscopin 1 peptide is highlighted darkly on the background (SEQ ID NO:3). The methionine start site and the putative C-terminal amidation donor residue are in bold letters.

FIG. 1B. Nucleic acid sequence and amino acid sequence of stresscopin 2 (SEQ ID NOS:4-5). The pre-pro region of stresscopin 2 peptide is 96 amino acids and is lightly shaded, while the putative mature stresscopin 2 peptide is shaded darkly (SEQ ID NO:6).

FIG. 1C. Comparison of the mature regions of CRH-related peptides from mammals, fish, and frog. Amino acid numbering is given on the left. The putative secondary structures of these polypeptides are indicated above the upper row of the alignment. CRH, urocortin, urotensin I, and sauvagine shared a similar structure with an N-terminal random coil followed by an extended α-helix structure. In contrast, the N-terminal sequences of human and pufferfish stresscopin peptides adopted an extended strand structure followed by a short random coil. Lightly shaded residues are conserved in the majority of aligned sequences. Residues that are identical in peptides of each subgroup are highlighted by a dark background. The legend is h is human; m is mouse; g is goldfish (*Carassius auratus*); s is sucker (Catostomus commersoni); f is leaf frog (Phyllomedusa sauvagei); and p is Fugu pufferfish (Takifugu rubripes). CRH family peptides all have a stretch of 30 residues at their C-termini and adopt an extended α-helical structure. Alignment of the mature pepetides with elevated CRH family hormones indicated that mature stresscopins from human and pufferfish, but not the pre-pro regions show 35-38% identity to other family proteins. SEQ ID NOS:4, 6-15.

FIG. 1D. Phylogenetic tree of CRH family proteins from vertebrates. Phylogenetic inference based on mature regions of CRH family proteins. Phylogenetic analysis of nine CRH family proteins from fish, frog and mammals suggests the ancient evolution of three subgroups of CRH family proteins, with the human and pufferfish stresscopins clustered in a separate branch.

FIG. 2. Expression of stresscopin transcripts and proteins.

FIG. 3. Stresscopin 1 and stresscopin 2 preferentially activate CRH R2. Hormonal stimulation of cAMP production by FIG. 3a. CRHR2-containing rat cardiac A7r5 cells, FIG. 3b. CRHR1-containing human retinoblastoma Y79 cells, FIG. 3c. recombinant CRHR2, FIG. 3d. recombinant CRHR2 and, FIG. 3e. recombinant CRHR1. Cells incubated with the test peptide or vehicle were harvested at 16 h after treatment and heated to 95° C. for 5 min to inactivate phosphodiesterase activity before cAMP measurement.

DESCRIPTION OF THE SPECIFIC EMBODIMENTS

Figure 2A:
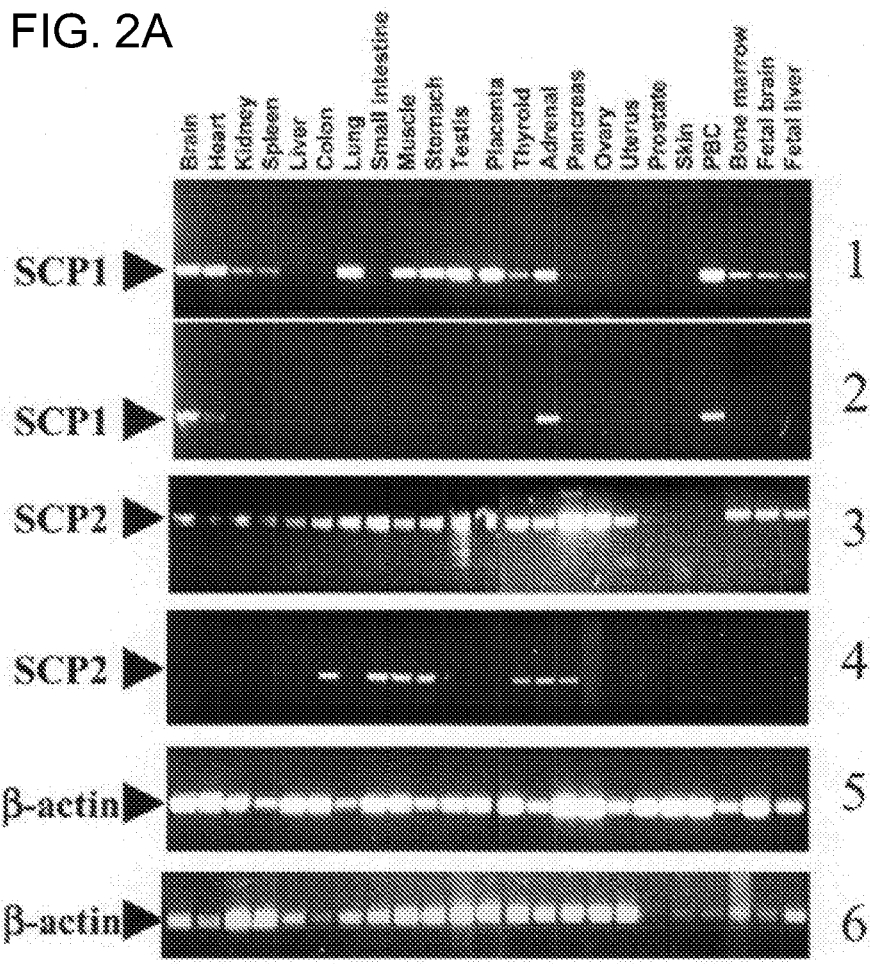
FIG. 2a, Expression of the stresscopin 1 (panels 1 and 2) and stresscopin 2 (panels 3 and 4) transcripts in 23 different human tissues as determined by PCR amplification. The specific cDNA bands are indicated by an arrowhead on the left. PCR products from experiments using two different concentrations of cDNA templates (1 ng template/reaction, panels 1 and 3; 10 pg template/reaction, panels 2 and 4) are shown. PBL, peripheral blood cells. The expression of -actin transcripts in cDNA templates from different tissues are shown in panels 5 (1 ng template/reaction) and 6 (10 pg template/reaction).

The invention provides novel nucleic acids and polypeptides, referred to herein as stresscopin 1 and stresscopin 2, which are members of the corticotropin releasing hormone family. Because stresscopins preferentially activate the CRH-R2 receptor over the R1 receptor, stresscopins, analogs and mimetics, and related CRH-R2 agonists suppress heat-induced edema as the result of their hypotensive actions as well as food intake; but do not induce substantial release of ACTH. Stresscopin also finds use in the recovery phase of stress responses, as an anti-inflammatory agent, as a cardioprotective agent, and in the treatment of psychiatric and anxiolytic disorders.

The nucleic acid compositions of the subject invention find use in identifying homologous or related genes; for production of the encoded protein; in producing compositions that modulate the expression or function of its encoded protein; for gene therapy; mapping functional regions of the protein; and in studying associated physiological pathways. In addition, modulation of the gene activity in vivo is used for prophylactic and therapeutic purposes. The proteins are useful as a therapeutic, as an immunogen for producing specific antibodies, in screening for biologically active agents that act in the CRH signaling pathways and for therapeutic and prophylactic purposes.

Stresscopins are natural agonists of the CRH-R2 receptor, where the term "agonist" refers to a compound that binds to, and activates a receptor. Compounds that inhibit this effect are referred to as "antagonists." Ligands, e.g. variants, derivatives and mimetics of stresscopins, may evoke a spectrum of responses ranging from full CRH-R2 activation by agonists to partial activation and inhibition by partial or complete antagonists.

Stresscopin Polypeptides

The mature stresscopin 1 polypeptide is a 43 amino acid peptide, derived from a 112 amino acid precursor protein. The amino acid sequence of the precursor protein and mature protein are provided as SEQ ID NO:2 and SEQ ID NO:3, respectively. The nucleotide sequence of the human stresscopin 1 cDNA is provided as SEQ ID NO:1. The mature stresscopin 2 is a peptide of 40 amino acids, derived from a 161 precursor protein. The amino acid sequence of the precursor protein and mature protein are provided as SEQ ID NO:5 and SEQ ID NO:6. The nucleotide sequence of stresscopin 2 is provided as SEQ ID NO:4.

Both human stresscopin ORFs contain a signal peptide for secretion and the predicted mature regions are flanked by potential proteolytic cleavage sites and an α-amidation donor residue. The identity of the stresscopin 1 and 2 transcripts was confirmed following PCR of cDNA from human testis and colon, respectively.

For use in the subject methods, either of the native stresscopin forms, modifications thereof, or a combination of forms may be used. Peptides of interest include fragments of at least about 12 contiguous amino acids, more usually at least about 20 contiguous amino acids, and may comprise 30 or more amino acids, up to the provided peptide, and may extend further to comprise other sequences present in the precursor protein.

A fragment of a stresscopin peptide may be selected to achieve a specific purpose. For example, deletions at the amino terminus of peptides having binding affinity for CRH-receptors have the effect of turning an agonist peptide into an antagonist, by retaining the receptor binding activity, but deleting the activation activity (for example, see Ruhmann et al. (1998) P.N.A.S. USA 95:15264-15269). Such deletions generally extend from residue 1 through 10 of the peptide, and may further delete additionally amino acids at residues 11, 12 or more. Smaller deletions, of from 1 to to 5 amino acids, may be deleted in the N-terminus and still retain the agonist properties.

The sequence of the stresscopin polypeptide may be altered in various ways known in the art to generate targeted changes in sequence. The polypeptide will usually be substantially similar to the sequences provided herein, i.e. will differ by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject invention are polypeptides that have been modified using ordinary molecular biological techniques and synthetic chemistry so as to improve their resistance to proteolytic degradation or to optimize solubility properties or to render them more suitable as a therapeutic agent. For examples, the backbone of the peptide may be cyclized to enhance stability (see Friedler et al. (2000) J. Biol. Chem. 275:23783-23789). Analogs of such polypeptides include those containing residues other than naturally occurring L-amino acids, e.g. D-amino acids or non-naturally occurring synthetic amino acids.

The subject peptides may be prepared by in vitro synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Compound Screening

The availability of purified stresscopin and other components in the signaling pathways, e.g. CRH-R1, CRH-R2, etc., allows in vitro reconstruction of the pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other, etc. The components may be modified by sequence deletion, substitution, etc. to determine the functional role of specific residues.

Drug screening may be performed using an in vitro model, a genetically altered cell or animal, or purified stresscopin protein. One can identify ligands or substrates that compete with, modulate or mimic the action of stresscopin. Areas of investigation include the development of treatments for suppression of food intake; suppression of edema; enhancing the recovery phase of stress responses; as an anti-inflammatory agent; as a cardioprotective agent; in the treatment of psychiatric and anxiolytic disorders, etc.

Drug screening identifies agents that mimic stresscopin activity, either as an antagonist or as an agonist. A wide variety of assays may be used for this purpose, including labeled in vitro protein-protein binding assays, electrophoretic mobility shift assays, immunoassays for protein binding, and the like. Knowledge of the 3-dimensional structure of stresscopin, derived from crystallization of purified synthetic stresscopin protein, leads to the rational design of small drugs that specifically inhibit stresscopin activity.

The term "agent" as used herein describes any molecule, e.g. protein or pharmaceutical, with the capability of altering or mimicking the physiological function of stresscopin. Generally, a plurality of assay mixtures are run in parallel with different agent concentrations to obtain a differential response to the various concentrations. Typically one of these concentrations serves as a negative control, i.e., at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

For example, a number of molecules have been described as antagonists or as agonists of CRH receptors. Screening assays that utilize stresscopin permit the improved selection for compounds having a desired specificity, of acting specifically on CRH-R2. Examples of such CRH agonists and antagonists include, among others, arylamino fused pyrimidines (U.S. Pat. No. 6,107,300); thiazolo[4,5-d]pyrimidines and pyridines (U.S. Pat. No. 6,107,294); pyrazoles and pyrazolopyrimidines (U.S. Pat. No. 6,103,900); aryl- and arylamino- substituted heterocycles (U.S. Pat. No. 6,103,737); tetrahydropteridines (U.S. Pat. No. 6,083,948); benzimidazole derivatives (U.S. Pat. No. 6,022,978); substituted 4-phenylaminothiazoles (U.S. Pat. No. 5,880,135); benzo(e)perimidine-4-carboxamide derivatives (U.S. Pat. No. 5,861,398); etc.

Also of interest are cyclic stresscopin analogs (see U.S. Pat. No. 5,663,292). Certain cyclic analogs, e.g. of CRH, have been found to act as antagonists, and have substantially no residual agonist activity. These peptides may have a cyclizing bond initiating, e.g. at the residues in the 32-position and may optionally have a second such bond initiating, e.g. at the residues in the 19- or the 20-positions. Either or both of these bonds may be an amide bond (or lactam bridge) between side chain carboxyl and amino groups. Alternative antagonists include fragments of the stresscopin sequence, as previously described.

The compounds having the desired pharmacological activity may be administered in a physiologically acceptable carrier to a host for treatment of stress related disorders, etc. The compounds may also be used to enhance stresscopin function in weight reduction, treatment of heart disease, reduction of edema, suppression of anxiety, stress reduction following major surgery, etc. The inhibitory agents may be administered in a variety of ways, orally, topically, parenterally e.g. subcutaneously, intraperitoneally, by viral infection, intravascularly, etc. Depending upon the manner of introduction, the compounds may be formulated in a variety of ways. The concentration of therapeutically active compound in the formulation may vary from about 0.1-10 wt %.

Antibodies Specific For Stresscopin Polypeptides

The present invention provides antibodies specific for stresscopin polypeptides, e.g. any one of the variants, polypeptides, or domains described above. Such antibodies are useful, for example, in methods of detecting the presence of stresscopin in a biological sample, and in methods of isolating stresscopin from a biological sample.

The stresscopin polypeptides of the invention are useful for the production of antibodies, where short fragments provide for antibodies specific for the particular polypeptide, and larger fragments or the entire protein allow for the production of antibodies over the surface of the polypeptide. As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme that generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

"Antibody specificity", in the context of antibody-antigen interactions, is a term well understood in the art, and indicates that a given antibody binds to a given antigen, wherein the binding can be inhibited by that antigen or an epitope thereof which is recognized by the antibody, and does not substantially bind to unrelated antigens. Methods of determining specific antibody binding are well known to those skilled in the art, and can be used to determine the specificity of antibodies of the invention for a stresscopin polypeptide, particularly a human stresscopin polypeptide.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see Monoclonal Antibodies: A Laboratory Manual, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage display libraries, usually in conjunction with in vitro affinity maturation.

Uses of Stresscopin

In light of the pharmacologic activities of stresscopin, numerous clinical indications are evident. For example, clinical indications for which a stresscopin peptide or variants thereof may find use include treatment of obesity, reduction of edema; as an anti-inflammatory agent, as a cardioprotective agent, as a hypotensive agent, as a stress-reducing agent, and in the treatment of psychiatric and anxiolytic disorders.

Human obesity is a widespread and serious disorder, affecting a high percentage of the adult population in developed countries. In spite of an association with heart disease, type II diabetes, cancer, and other conditions, few persons are able to permanently achieve significant weight loss. The subject peptides are administered to obese patients for purposes of appetite suppression. Patients may use various criteria for determining obesity. Conveniently, a body mass index (BMI) is calculated, where a person having a BMI greater than 25 is overweight and may considered for treatment with the subject peptides. Stresscopins find use in promoting gastric stasis and anorexic behavior without concomitant activation of the ACTH-glucocorticoid axis.

In a related embodiment, the treatment of non-insulin-dependent diabetes mellitus (NIDDM) is closely related to the treatment of obesity. NIDDM is a metabolic disease that affects about 5% to 7% of the population in western countries (and 10% of individuals over age 70). It is characterized by hyperglycemia and often accompanied by a number of other conditions, including hypertension, obesity and lipid disturbances. Patients are generally categorized as diabetic or hyperglycemic by measuring the level of glucose in the blood, either directly or by monitoring the level of glycosylated hemoglobin. Treatment is recommended where fasting glucose levels are greater 140 mg/dl, where bedtime glucose is greater than 160 mg/dl, or where $HbA_{1c}$ is greater than 8%. The level of reduction that is desirable depends on the condition of the patient, and the blood glucose levels at the start of treatment, but generally about a 10 to 40% reduction is blood glucose is desirable, usually about a 25 to 35% reduction.

The effects of stresscopins on stress related disorders provides a means of treating affective and mood disorders, which are a group of mental disorders characterized by neuroendocrine dysregulation and are characterized by a disturbance in the regulation of mood, behavior, and affect. Affective and mood disorders can have serious impact on an individual's functional ability, interpersonal relationships and behavior. Neuroendocrine dysregulation, specifically changes in the hypothalamic-pituitary-adrenal (HPA) axis, has been investigated as a biological correlate of depression. Overall, the HPA axis regulates physiologic responses to stress. The hypothalamus controls endocrine functions and the autonomic nervous system. It is involved in behaviors related to fight, flight, feeding and mating, many of which are altered during episodes of depression.

The hypothalamus releases CRH and related peptides in response to stress, which then stimulates the anterior pituitary to secrete adrenocorticotrophichormone (ACTH). ACTH prompts the adrenal cortex to release cortisol which, through elaborate feedback mechanisms signals the hypothalamus to increase or decrease CRH production. Under ordinary circumstances, activation of hypothalamic CRH is terminated rapidly by the negative feedback of rising glucocorticoid levels. However, in melancholic depression, hypercortisolism does not adequately restrain the production of CRH in the hypothalamus. Thus, in melancholic depression, CRH levels are chronically elevated causing hyperactivity of the HPA axis. Through administration of stresscopins, the excessive release of ACTH is avoided.

Major depression is a syndromal, episodic and recurrent illness with both psychological and biological components. A diagnosis of bipolar disorder is given to those patients with recurring depression and mania. Those patients with recurrent depression alone have a unipolar pattern. Within the spectrum of depressive illness, there are two distinct subtypes: melancholic depression and atypical depression. Melancholic depression is equally common among those with a pattern of unipolar and bipolar depression. Melancholic depression is characterized by hyposomnia (early morning awakening), anorexia and diurnal variation in mood, and is associated with a state of hyperarousal. Atypical depression is more common in bipolar patients than in unipolar depressed patients. Atypical depression is characterized by a state which seems to be opposite to that of melancholic depression.

Patients with atypical depression have a syndrome of hypoarousal with hypersomnia, hyperphagia, weight gain and mood liability.

Dysthymia is a chronic disorder characterized by symptoms that include poor appetite or overeating, low energy (decreased arousal), insomnia or hypersomnia, and poor concentration. These functions are modulated by neuropeptides in the brain, such as CRH and stresscopins. Generally, dysthymia is characterized by hypothalamic CRH levels that are higher than normal, thereby causing hyperactivity of the HPA axis. However, in dysthymia, hypothalamic CRH levels can be lower than normal, causing hypoactivity of the HPA axis, in individuals with a higher than normal body mass index (BMI). Thus, in dysthymia, hypothalamic CRH levels are inversely related to the BMI of the individual.

Affective disorders are extremely common in general medical practice, as well as in psychiatry. The severity of these conditions covers an extraordinarily broad range, from normal grief reactions to severe, incapacitating, and sometimes fatal psychosis. Typically these disorders are treated with antidepressant agents or lithium salts. Nevertheless, many shortcomings and problems continue to be associated with all drugs used to treat affective disorders. In addition to less than-dramatic efficacy in some cases, virtually all the drugs used to treat disorders of mood are potentially lethal when acute over dosage occurs and can cause appreciable morbidity even with careful clinical use. Stresscopins find use as an anxiolytic agent.

Hypertension is a disease which, if untreated, strongly predisposes to atherosclerotic cardiovascular disease. It is estimated that as many as 1 in 4 adult Americans have hypertension. Hypertension is approximately twice as common in persons with diabetes as in those without. The prevalence of hypertension increases with age.

Hypertension should not be diagnosed on the basis of a single measurement. Initial elevated readings should be confirmed on at least two subsequent visits over one week or more with average diastolic blood pressure of 90 mmHg or greater or systolic blood pressure of 140 mmHg or greater required for diagnosis of hypertension. Special care is warranted in diagnosing hypertension in persons with diabetes because of greater variability of blood pressure and a much greater likelihood of isolated systolic hypertension. A goal blood pressure of less than 130/85 mmHg is recommended for these patients.

In addition to dietary changes, pharmacological treatment may be required to control high blood pressure. The subject peptides may be administered to reduce arterial blood pressure. In addition. a secondary effect of reducing hypertension is reduction of edema and inflammatory exudate volume.

After substantial stress, e.g. major surgery, severe burn, emotional trauma, organ transplantation, and other life threatening situations, the subject peptides may be administered to enhance the stress coping responses. The regulation of the hypothalamo-pituitary-adrenal (HPA) axis in the operative and perioperative period of major surgical procedures is necessary for successful adaption to surgical stress. For example, plasma ACTH has been found to be highly elevated during a surgical procedure; which were temporally related to CRH levels. The immediate postoperative period may be associated with profound elevations of plasma ACTH, cortisol, and epinephrine. Results have indicated an altered regulation of the HPA axis in the postoperative period of patients after surgery, which are compatible with similar results in patients after major abdominal surgery, burned patients, and critically ill patients.

Pharmaceutical compositions containing stresscopin peptides and derivatives therefrom are useful as cardioprotective agents, e.g. to ameliorate ischemic injury or myocardial infarct size consequent to myocardial ischemia. The development of new therapeutic agents capable of limiting the extent of myocardial injury, i.e., the extent of myocardial infarction, following acute myocardial ischemia is a major concern of modern cardiology. There has also been interest in the development of therapies capable of providing additional myocardial protection which could be administered in conjunction with thrombolytic therapy, or alone, since retrospective epidemiological studies have shown that mortality during the first few years following infarction appears to be related to original infarct size.

Myocardial ischemia is the result of an imbalance of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone.

The compounds of this invention can be normally administered orally or parenterally, in the treatment of patients in need of cardioprotective therapy. The dosage regimen is that which insures maximum therapeutic response until improvement is obtained and thereafter the minimum effective level which gives relief. Thus, in general, the dosages are those that are therapeutically effective in producing a cardioprotective effect, i.e., amelioration of ischemic injury or myocardial infarct size consequent to myocardial ischemia. It is also anticipated that the peptides would be useful as an injectable dosage form which may be administered in an emergency to a patient suffering from myocardial ischemia, etc.

The prevention or inhibition of illness leading to inflammation is of significant concern, particularly for those afflicted with autoimmune diseases such as arthritis and different injuries, including sports-related injuries and musculoskeletal ailments. Pain usually accompanies inflammation and vice versa. Inflammation involves capillary dilation, with accumulation of fluid and migration of phagocytic leukocytes, such as granulocytes and monocytes, to the site of injury or lesion. Inflammation is important in defending a host against a variety of infections, but can also have undesirable consequences in inflammatory disorders. Inflammatory conditions include autoimmune diseases; inflammation caused by bacterial and viral infection, including response to vaccination; local inflammation in response to trauma; graft rejection; graft v. host disease, and the like. Stresscopin also finds use in the treatment of different skin diseases.

Conditions of interest for treatment with the subject peptides include musculoskeletal conditions, both inflammatory and non-inflammatory in nature, and acute, subacute or chronic presentation. For example, the composition may be used in the treatment of both the early and late stages of inflammatory arthritis, as well as non-infectious inflammatory arthropathy such as rheumatoid arthritis, bursitis, tendinitis, soft tissue injuries, Sjogren's syndrome, systemic lupus erythematous, psoriatic arthritis, gout and other crystalline arthropathies, capsulitis, carpal tunnel syndrome, myositis, polymyalgia, rheumatica, synovitis and Reiter's syndrome. The compositions of this invention may also be used in the prevention or treatment of erosive osteoarthritis. Acute and chronic pain and inflammation are often treated with anti-inflammatory/analgesic compounds such as aspirin, ibuprofen and naproxen. The subject peptides may find use in combinations with these compounds.

The stresscopin peptides and derivatives therefrom also find use in the reduction of edema, for example in rheumatoid arthritis, edema secondary to brain tumors or irradiation for cancer, edema resulting from stroke, head trauma or spinal cord injury, post-surgical edema, asthma and other respiratory diseases and cystoid macular edema of the eye.

Formulations

The compounds of this invention can be incorporated into a variety of formulations for therapeutic administration. Particularly, agents that modulate stresscopin activity, or stresscopin polypeptides and analogs thereof are formulated for administration to patients for the treatment of stresscopin dysfunction, where the stresscopin activity is undesirably high or low. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The stresscopin may be systemic after administration or may be localized by the use of an implant that acts to retain the active dose at the site of implantation.

In pharmaceutical dosage forms, the compounds may be administered in the form of their pharmaceutically acceptable salts, or they may also be used alone or in appropriate association, as well as in combination with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of infection, so that the local concentration of active agent is increased relative to the rest of the body.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 μg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like.

For preparing the liposomes, the procedure described by Kato et al. (1991) *J. Biol. Chem.* 266:3361 may be used. Briefly, the lipids and lumen composition containing the nucleic acids are combined in an appropriate aqueous medium, conveniently a saline medium where the total solids will be in the range of about 1-10 weight percent. After intense agitation for short periods of time, from about 5-60 sec., the tube is placed in a warm water bath, from about 25-40° C. and this cycle is repeated about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

For use in the above described formulations, stresscopin or derivatives therefrom may be synthesized and stored as a solid lyophilized powder which is reconstituted into a pharmaceutically acceptable liquid immediately prior to use. Such formulations are usually preferred because it is recognized by those skilled in the art that lyophilized preparations generally maintain pharmaceutical activity better over time than their liquid counterparts.

In addition, stresscopins and their analogs could be applied topically on the skin as well as administered as aerosol sprays.

Alternatively, the peptides may be formulated as a liquid, e.g. comprising a buffer at a concentration of from about 1 mM to about 50 mM that functions to maintain the pH, wherein the anion of said buffer may be selected from the group consisting of acetate, phosphate, carbonate, succinate, citrate, borate, tartrate, fumarate and lactate; and an alcohol which may be selected from the group consisting of mannitol, sorbitol, ribotol, arabitol, xylitol, inositol, galactitol, methanol, ethanol and glycerol. Other additives may include amino acids such as methionine, arginine, lysine, glutamic acid, cysteine, glutathione, and the like, where amino acids are generally present in concentrations ranging from about 1 mM to about 100 mM. Various sugars are optionally included in the formulations, including, for example, glucose, sucrose, lactose, fructose, trehalose, mannose, and the like. Additive sugars are generally present in concentrations ranging from about 1% to about 10%.

Stresscopin Nucleic Acids

The invention includes nucleic acids having a sequence set forth in SEQ ID NO:1 and SEQ ID NO:4; nucleic acids that hybridize under stringent conditions, particularly conditions of high stringency, to the sequences set forth in SEQ ID NO:1 and SEQ ID NO:2; genes corresponding to the provided nucleic acids; sequences encoding stresscopins; and fragments and derivatives thereof. Other nucleic acid compositions contemplated by and within the scope of the present invention will be readily apparent to one of ordinary skill in the art when provided with the disclosure here.

The nucleic acids of the invention include nucleic acids having sequence similarity or sequence identity to SEQ ID NO:1 and SEQ ID NO:4. Nucleic acids having sequence similarity are detected by hybridization under low stringency conditions, for example, at 50° C. and 10×SSC (0.9 M saline/ 0.09 M sodium citrate) and remain bound when subjected to washing at 55° C. in 1×SSC. Sequence identity can be determined by hybridization under stringent conditions, for example, at 50° C. or higher and 0.1×SSC (9 mM saline/0.9 mM sodium citrate). Hybridization methods and conditions are well known in the art, see, e.g., U.S. Pat. No. 5,707,829.

Nucleic acids that are substantially identical to the provided nucleic acid sequence, e.g. allelic variants, genetically altered versions of the gene, etc., bind to SEQ ID NO:1 or SEQ ID NO:4 under stringent hybridization conditions. By using probes, particularly labeled probes of DNA sequences, one can isolate homologous or related genes. The source of homologous genes can be any species, e.g. primate species, particularly human; rodents, such as rats and mice; canines, felines, bovines, ovines, equines, fish, yeast, nematodes, etc.

In one embodiment, hybridization is performed using at least 18 contiguous nucleotides (nt) of SEQ ID NO:1 and SEQ ID NO:4, or a DNA encoding the polypeptide of SEQ ID NO:2, SEQ ID NO:3, SEQ ID NO:5 or SEQ ID NO:6. Such a probe will preferentially hybridize with a nucleic acid comprising the complementary sequence, allowing the identification and retrieval of the nucleic acids that uniquely hybridize to the selected probe. Probes of more than 18 nt can be used, e.g., probes of from about 18 nt to about 25, 50, 100, 250, or 500 nt, but 18 nt usually represents sufficient sequence for unique identification.

Nucleic acids of the invention also include naturally occurring variants of the nucleotide sequences (e.g., degenerate variants, allelic variants, etc.). Variants of the nucleic acids of the invention are identified by hybridization of putative variants with nucleotide sequences disclosed herein, preferably by hybridization under stringent conditions. For example, by using appropriate wash conditions, variants of the nucleic acids of the invention can be identified where the allelic variant exhibits at most about 25-30% base pair (bp) mismatches relative to the selected nucleic acid probe. In general, allelic variants contain 15-25% bp mismatches, and can contain as little as even 5-15%, or 2-5%, or 1-2% bp mismatches, as well as a single bp mismatch.

The invention also encompasses homologs corresponding to the nucleic acids of SEQ ID NO:1 and SEQ ID NO:4, or a DNA encoding the polypeptide of SEQ ID NO:2, SEQ ID NO:3, SEQ ID NO:5 or SEQ ID NO:6, where the source of homologous genes can be any mammalian species, e.g., primate species, particularly human; rodents, such as rats; canines, felines, bovines, ovines, equines, fish, yeast, nematodes, etc. Between mammalian species, e.g., human and mouse, homologs generally have substantial sequence similarity, e.g., at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 contiguous nt long, more usually at least about 30 nt long, and may extend to the complete sequence that is being compared. Algorithms for sequence analysis are known in the art, such as gapped BLAST, described in Altschul et al. *Nucl. Acids Res.* (1997) 25:3389-3402.

The subject nucleic acids can be cDNAs or genomic DNAs, as well as fragments thereof, particularly fragments that encode a biologically active polypeptide and/or are useful in the methods disclosed herein (e.g., in diagnosis, as a unique identifier of a differentially expressed gene of interest, etc.). The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' and 3' end of the transcribed region. The genomic DNA can be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue, stage-specific, or disease-state specific expression.

The nucleic acid compositions of the subject invention can encode all or a part of the subject polypeptides. Double or single stranded fragments can be obtained from the DNA sequence by chemically synthesizing oligonucleotides in accordance with conventional methods, by restriction enzyme digestion, by PCR amplification, etc. Isolated nucleic acids and nucleic acid fragments of the invention comprise at least about 18, about 50, about 100, to about 500 contiguous nt selected from the nucleic acid sequence as shown in SEQ ID NO:1 and SEQ ID NO:4. For the most part, fragments will be of at least 18 nt, usually at least 25 nt, and up to at least about 50 contiguous nt in length or more.

Probes specific to the nucleic acid of the invention can be generated using the nucleic acid sequence disclosed in SEQ ID NO:1 and SEQ ID NO:4, or a DNA encoding the polypeptide of SEQ ID NO:2, SEQ ID NO:3, SEQ ID NO:5 or SEQ ID NO:6. The probes are preferably at least about 18 nt, 25 nt or more of the corresponding contiguous sequence. The probes can be synthesized chemically or can be generated from longer nucleic acids using restriction enzymes. The probes can be labeled, for example, with a radioactive, biotinylated, or fluorescent tag. Preferably, probes are designed based upon an identifying sequence of one of the provided sequences. More preferably, probes are designed based on a contiguous sequence of one of the subject nucleic acids that remain unmasked following application of a masking program for masking low complexity (e.g., BLASTX) to the sequence, i.e., one would select an unmasked region, as indicated by the nucleic acids outside the poly-n stretches of the masked sequence produced by the masking program.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Modulation of Stresscopin Expression

The stresscopin genes, gene fragments, or the encoded protein or protein fragments are useful in gene therapy to treat disorders associated with stresscopin defects. From a therapeutic point of view, inhibiting stresscopin activity has a therapeutic effect on a number of disorders relating to stress. Inhibition is achieved in a number of ways. Antisense stresscopin sequences may be administered to inhibit expression. Competitive binding antagonists, for example, a peptide that mimics stresscopin binding may be used to inhibit activity. Other inhibitors are identified by screening for biological activity in a stresscopin-based binding assay.

Expression vectors may be used to introduce the stresscopin gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or stresscopin peptide may be introduced into tissues or host cells by any number of routes, including viral infection, microinjection, or fusion of vesicles. Jet injection may also be used for intramuscular administration, as described by Furth et al. (1992) Anal Biochem 205:365-368. The DNA may be coated onto gold microparticles, and delivered intradermally by a particle bombardment device, or "gene gun" as described in the literature (see, for example, Tang et al (1992) Nature 356:152-154), where gold microprojectiles are coated with the stresscopin or DNA, then bombarded into skin cells.

Antisense molecules can be used to down-regulate expression of stresscopin in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in vitro or in an animal model. A combination of sequences may also be used, where several regions of the mRNA sequence are selected for antisense complementation.

Antisense oligonucleotides may be chemically synthesized by methods known in the art (see, Wagner et al. (1993), supra and Milligan et al., supra). Preferred oligonucleotides are chemically modified from the native phosphodiester structure, in order to increase their intracellular stability and binding affinity. A number of such modifications have been described in the literature which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 95/23225, and Beigelman et al. (1995) *Nucl. Acids Res.* 23:4434-4442). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl. Biochem. Biotechnol.* 54:43-56.

Agents that block stresscopin activity provide a point of intervention in an important signaling pathway. Numerous agents are useful in reducing stresscopin activity, including agents that directly modulate stresscopin expression as described above, e.g. expression vectors, anti-sense specific for stresscopin; and agents that act on the stresscopin protein, e.g. stresscopin specific antibodies and analogs thereof, small organic molecules that block stresscopin binding activity, etc.

Diagnostic Uses

DNA-based reagents derived from the sequence of stresscopins, e.g. PCR primers, oligonucleotide or cDNA probes, as well as antibodies against stresscopins, are used to screen patient samples, e.g. biopsy-derived tissues, blood samples, etc., for amplified stresscopin DNA, or increased expression of stresscopin mRNA or proteins. DNA-based reagents are also designed for evaluation of chromosomal loci implicated in certain diseases e.g. for use in loss-of-heterozygosity (LOH) studies, or design of primers based on stresscopin coding sequence.

The polynucleotides of the invention can be used to detect differences in expression levels between two samples. A difference between the protein levels, or the mRNA in the two tissues that are compared, for example, in molecular weight, amino acid or nucleotide sequence, or relative abundance, indicates a change in the gene, or a gene which regulates it, in the tissue of the human that was suspected of being diseased.

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in a stresscopin coding region or control regions is associated with disease, particularly stress related disorders, e.g. anxiety disorders. Disease associated polymorphisms may include deletion or truncation of the gene, mutations that alter expression level, that affect the binding activity of the protein, the kinase activity domain, etc.

Changes in the promoter or enhancer sequence that may affect expression levels of stresscopin can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express stresscopin may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. Molecular Cloning: A Laboratory Manual, CSH Press 1989, pp. 14.2-14.33.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein(6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g., amplified or cloned fragment, is analyzed by one of a number of methods known in the art. The nucleic acid may be sequenced by dideoxy or other methods, and the sequence of bases compared to a wild-type stresscopin sequence. Hybridization with the variant sequence may also be used to determine its presence, by Southern blots, dot blots, etc. The hybridization pattern of a control and variant sequence to an array of oligonucleotide probes immobilized on an array, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in stresscopins may be based on the functional or antigenic characteristics of the protein. Protein truncation assays are useful in detecting deletions that may affect the biological activity of the protein. Various immunoassays designed to detect polymorphisms in stresscopin proteins may be used in screening. Where many diverse genetic mutations lead to a particular disease phenotype, functional protein assays have proven to be effective screening tools. The activity of the encoded stresscopin protein in binding assays, etc., may be determined by comparison with the wild-type protein. Proteins may also be screened for the presence of post-translational modification of the stresscopin proteins, e.g. under pathological conditions, including proteolytic fragments, amidation, acetylation etc.

Antibodies specific for stresscopin may be used in staining or in immunoassays. Samples, as used herein, include biological fluids such as blood, cerebrospinal fluid, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal stresscopin in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

In some embodiments, the methods are adapted for use in vivo. In these embodiments, a detectably-labeled moiety, e.g., an antibody, which is specific for stresscopin is administered to an individual (e.g., by injection), and labeled cells are located using standard imaging techniques, including, but not limited to, magnetic resonance imaging, computed tomography scanning, and the like.

Diagnostic screening may also be performed for polymorphisms that are genetically linked to a disease predisposition, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) *Genomics* 24:225-233; Ziegle et al. (1992) *Genomics* 14:1026-1031; Dib et al., supra.

Diagnostic screening may also be performed for polymorphisms that are genetically linked to a predisposing mutation, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994) *Genomics* 24:225-233; Ziegle et al. (1992) *Genomics* 14:1026-1031; Dib et al., supra.

The detection methods can be provided as part of a kit. Thus, the invention further provides kits for detecting the presence of an mRNA encoding stresscopin, and/or a polypeptide encoded thereby, in a biological sample. Procedures using these kits may be performed by clinical laboratories, experimental laboratories, medical practitioners, or private individuals. The kits of the invention for detecting a polypeptide comprise a moiety that specifically binds the polypeptide, which may be a specific antibody. The kits of the invention for detecting a nucleic acid comprise a moiety that specifically hybridizes to such a nucleic acid. The kit may optionally provide additional components that are useful in the procedure, including, but not limited to, buffers, developing reagents, labels, reacting surfaces, means for detection, control samples, standards, instructions, and interpretive information.

Genetically Altered Cell Or Animal Models For Stresscopin Function

The subject nucleic acids can be used to generate transgenic animals or site specific gene modifications in cell lines. Transgenic animals may be made through homologous recombination, where the normal stresscopin locus is altered. Alternatively, a nucleic acid construct is randomly integrated into the genome. Vectors for stable integration include plasmids, retroviruses and other animal viruses, YACs, and the like.

The modified cells or animals are useful in the study of stresscopin function and regulation. For example, a series of small deletions and/or substitutions may be made in the stresscopin gene to determine the role of different residues in receptor binding, signal transduction, etc. Of interest is the use of stresscopin to construct transgenic animal models for stress related disorders, where expression of stresscopin is specifically reduced or absent. Specific constructs of interest include anti-sense stresscopin, which will block stresscopin expression and expression of dominant negative stresscopin mutations. A detectable marker, such as lac Z may be introduced into the stresscopin locus, where up-regulation of stresscopin expression will result in an easily detected change in phenotype.

One may also provide for expression of the stresscopin gene or variants thereof in cells or tissues where it is not normally expressed or at abnormal times of development. By providing expression of stresscopin protein in cells in which it is not normally produced, one can induce changes in cell behavior, e.g. in the control of cell growth and tumorigenesis.

DNA constructs for homologous recombination will comprise at least a portion of the stresscopin gene with the desired genetic modification, and will include regions of homology to the target locus. The regions of homology may include coding regions, or may utilize intron and/or genomic sequence. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) Methods in Enzymology 185:527-537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in culture. The transgenic animals may be any non-human mammal, such as laboratory animals, domestic animals, etc. The transgenic animals may be used in functional studies, drug screening, etc., to determine the effect of a candidate drug on stress responses.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Materials And Methods

Cloning, Sequencing And Expression Analysis of Human Stresscopin cDNA

The identity of stresscopin 1 mRNA was deduced by comparisons of multiple human genomic DNA sequences (AC024179 and AC005903) and a partial EST sequence (BE390203). The deduced ORF of stresscopin 1 was verified by PCR using nested gene-specific primers and Marathon-ready cDNA templates (Clontech, Inc., Palo Alto, Calif.) from human testis and prostate. Stresscopin 2 was initially identified as a partial cDNA (AW293249) from a human subtracted library NC_CGAP_Sub4. The identity of this gene was verified by rapid amplification of 3' cDNA ends using a human Marathon-ready colon cDNA library.

Amplified cDNA fragments were gel-purified and subcloned following blunt-end ligation. To determine the expression profile of the stresscopin 1 gene, stresscopin transcript in 23 human tissues was amplified by high stringency PCR using a panel of genomic DNA-free first strand cDNAs primed with oligo-d(T) primer (Origene Technologies, Inc., Rockville, Md.) as template.

Immunohistochemical analysis. Specific rabbit anti-stresscopin 1 and anti-stresscopin 2 antibodies were generated using synthetic peptides corresponding to the mature region of stresscopin 1 and stresscopin 2, respectively, as the antigen (Strategic Biosolutions, Ramona, Calif.). The stresscopin peptides were conjugated to the carrier protein keyhole limpet hemocyanin using 1-ethyl-3-(3-dimethylaminopropyl)carbodiimide hydrochloride before immunization. Antibodies were purified using antigen-conjugated affinity columns and their titers determined by ELISA.

Tissues were obtained from adult male mice and embedded in paraffin following fixation in Bouin's solution. Following incubation in xylene, tissue sections were blocked with 5% goat serum in PBS to saturate nonspecific binding sites. Sections were then incubated with the specific anti-stresscopin antibody for 2 h at room temperature in a moist chamber before washing for three times (20 min each) in PBS with 0.1% Tween 20. Following incubation with the primary antibody, sections were incubated with gold-conjugated goat anti-rabbit IgG. Sections were then washed before being stained with the SilvEnhance solution (Zymed Laboratory, Inc., South San Francisco, Calif.) and counterstained with hematoxylin. Negative controls were performed by substituting the primary antibodies with antibodies presaturated with the peptide antigen.

Peptide synthesis and analysis. The stresscopin peptides with greater than 95% purity were synthesized using a Symphony/Multiplex™ automated peptide synthesizer based on the solid phase fluorenylmethoxycarbonyl protocol. All peptides synthesized were routinely analyzed by reverse phase HPLC with a Vydac C18 analytical column and Mass Spectrometry using a MALDI-TOF (matrix-assisted laser desorption ionization-time of flight) Voyager-DE RP Biospectrometry Workstation. Full-length stresscopin prepared with this protocol agrees with a calculated 4691 MW of the amidated form of stresscopin. CRH and urocortin were purchased from Sigma Biochemicals, Inc. (St Louis, Mo.). Astressin was purchased from Bachem Feinchemicalien, Bubendorf, Switzerland. Radiolabeled [$^{125}$I] human urocortin (2000 Cu/mmole) tracer was purchased from Amersham Pharmacia (Arlington Heights, Ill.).

Construction of Expression Vectors For CRH Receptors And the cAMP Assay

To obtain full-length type I and type II CRH receptor cDNAs for functional assays, nested gene-specific primers flanking the receptor ORF were used to PCR full-length cDNA fragments of CRH R1, CRH R2-α, and CRH R2β receptors. The receptor cDNA fragments were subcloned into the pcDNA3.1/Zeo vector with a prolactin signal peptide for secretion and triple FLAG/M1 epitope cassette upstream of the multiple cloning site. CRH receptor expression vectors were transfected into human 293T cells under serum-free conditions for 2 h followed by incubation in DMEM/F12 medium with 10% fetal bovine serum (FBS) for another 48 h. For the estimation of adenylate cyclase activation by stresscopin and related hormones, transfected cells were seeded at a concentration of 100,000 cell/well in 48 well culture plates in DMEM/F12 medium containing 0.1% BSA and 2.5 mM IBMX for 16 h. Contents of cAMP in whole cell lysate were determined using a cAMP radioimmunoassay. To analyze the effects of stresscopin and related hormones on cAMP accumulation in cells constitutively expressing CRH receptors, a human retinoblastoma cell line (Y79) and a rat cardiac cell line (A7r5) were purchased from ATCC (Manassas, Va.) and maintained in DMEM/F12 medium with 20% FBS before treatment with different hormones.

Phylogenetic inference. A multiple alignment of selected vertebrate CRH family protein sequences was constructed with ClustalX and corrected using a published alignment of mature protein data. Phylogenetic analysis was carried out by the neighboring-joining method as well as the BlockMaker using Gibbs method.

Receptor Binding assay. Human 293T cells expressing different isoforms of CRH R2 were incubated with 50,000 cpm (0.1 g) of $^{125}$I-urocortin and various concentrations of nonradioactive peptides diluted in a binding buffer consisting of PBS, a protease inhibitor cocktail (Sigma Biochemicals, Inc.), and 0.1% BSA. After 60 min incubation at 37° C., the cell-associated ligand was estimated following centrifugation and repeated washing. Radioactivity of samples was determined in a GENESYS-counter (Laboratory Technologies, Inc., Maple Park, Ill.).

Food intake and body weight in food-restricted mice. Six week-old male mice (20-25 g b.w.) of the inbreed Balb/C strain were housed individually in a regulated environment with 12L/12D light cycle. Before feeding tests, mice were deprived of food for 16 h with free access to water and injected with testing reagents i.p. at 10 AM the following day. Food intake was measured by placing preweighed pellets in the cage and weighing the uneaten pellets at 2, 4 and 8 h after injection. Body weight was also monitored at 0, 2, 4, and 8 h.

Effects on gastric emptying in food-restricted mice. To study the effects on gastric emptying, mice were deprived of food for 16 h with free access to water. The fasted mice were then given free access to preweighed pellets for 90 min. and were injected i.p. with different hormones or saline. The mice were deprived of food again after i.p. injection and sacrificed by cervical dislocation at 2 h. after injection. The stomach was excised at point of the pylorus and cardia before determination of its wet weight. Gastric emptying was calculated by comparison with stomach weight of control mice sacrificed at 0 h. following injection. See, Asakawa, A. et al. (1999) *Gastroenterology* 116:1287-1292.

Effects on heat-induced paw edema formation in anaesthetized rats. The anti-inflammatory effect of stresscopin and related peptides were assayed using an established model (Turnbull et al. (1996) *Euro. J. Pharmacol.* 303:213-216). Briefly, 5-week-old male Sprague-Dawley rats were injected with 20 nM of the testing peptide and anaesthetized with ketamine (100 mg/Kg). Thirty min. later, paw edema was induced following a one minute exposure to hot water at 58° C. The animals were sacrificed 30 min later. Both paws were removed at the ankle joint and weighed. The degree of edema was estimated as the differences in weight gain between the heated and unheated paw divided by the weight of the unheated paw.

In Vivo and in Vitro assay of pituitary ACTH releasing activity. Anterior pituitaries were obtained from 6-week-old male Sprague-Dawley rats. Following dispersion using collagenase and mechanical pipetting, cells were resuspended and cultured for 3 days in DMEM with 10% FBS (2×10$^5$ cells/well). Before hormonal treatment, cells were washed twice with serum-free medium followed by incubation with DMEM/F12 media containing 0.1% BSA, 2.5 mM IBMX, and different hormones (1 nM). After 2 h at 37° C., media were collected and assayed for ACTH contents using a radioimmunoassay from Diagnostic Systems Laboratories, Inc. (Webster, Tex.). To detect the ACTH-releasing activity of stresscopins and related peptides in vivo, 6-week-old male Sprague-Dawley rats were injected with different hormones i.p. (2 nmoles/kg) and sacrificed 30 min following treatment. Whole blood was collected with 60 IU/ml heparin and serum obtained for ACTH measurement.

Results

As shown in FIG. 1, there is significant homology between the provided stresscopin sequences, and other genes in the corticitropin releasing hormone gene family. Two human paralogs of CRH/urocortin have been identified, stresscopin 1 and stresscopin 2. A putative stresscopin ortholog from Japanese pufferfish (Takifugu rubripes) is also identified. Stresscopin 1 encodes a prepro-protein of 112 amino acids and a putative mature protein of 43 amino acids whereas the 161-amino-acid open reading frame (ORF) of stresscopin 2 contains a predicted 41-amino-acid mature peptide (FIGS. 1a and 1b).

Although the overall amino acid sequences of stresscopins from human and fish showed no similarity to known proteins, a stretch of 30 residues at their C-termini adopted an extended α-helical structure shared by all CRH family peptides (FIG. 1c). Both human stresscopin ORFs contain a signal peptide for secretion. The predicted mature regions are flanked by potential proteolytic cleavage sites and an alpha-amidation donor residue. The identity of stresscopin 1 and stresscopin 2 transcripts was confirmed following PCR of cDNAs from human testis and colon, respectively.

Alignment of the mature peptides with related CRH family hormones indicated that mature stresscopins from human and pufferfish, but not the prepro-regions, show 35-38% identity to other family proteins (FIG. 1c). These novel peptides share identical secondary structures, although the predicted structures of mature stresscopin 1 and stresscopin 2 are distinct from that of other family peptides at their N-terminus (FIG. 1c). Phylogenetic analysis of nine CRH family proteins from fish, frog, and mammals suggested the ancient evolution of three subgroups of CRH family proteins, with the human and pufferfish stresscopins clustered in a separate branch (FIG. 1d).

Based on PCR analysis using a panel of human cDNAs (1 ng/reaction) from 23 different tissues, stresscopin 1 transcript was found in brain and multiple peripheral tissues (heart, kidney, spleen, lung, muscle, stomach, testis, placenta, thyroid, adrenal, pancreas, ovary, peripheral blood cells, bone marrow, and fetal liver) (FIG. 2a, panel 1). The same analysis using diluted template cDNA (10 pg/reaction) shows the stresscopin 1 transcript only in brain, heart, adrenal, and peripheral blood cells, suggesting a relatively greater abundance of stresscopin 1 expression in these tissues (FIG. 2a, panel 2).

Likewise, PCR analysis showed that the stresscopin 2 transcript could be detected in most tissues analyzed with colon, small intestine, muscle, stomach, thyroid, adrenal, and pancreas showing greater levels of expression (FIG. 2a, panels 3 and 4). Because heart and digestive tissues showed relatively higher expression of the stresscopin 1 and stresscopin 2 transcripts, respectively, a comparative analysis was performed for stresscopin 1 mRNA in different cardiac compartments and stresscopin 2 transcript in the digestive system.

Figure 2B:
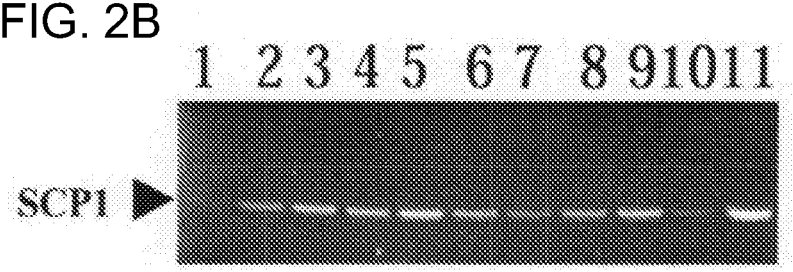
FIG. 2b. Expression of the stresscopin 1 transcript in 11 different human cardiac compartments as determined by PCR amplification using a primer pair flanking part of the C-terminal ORF and the 3'-untranslated region of stresscopin 1 cDNA and 1 ng of template cDNA. Lane 1, atrioventricular node; lane 2, atrioventricular septum; lane 3, aorta; lane 4, apex of the heart; lane 5, left atrium; lane 6, right atrium; lane 7, dextra auricle; lane 8, sinistra auricle; lane 9, left ventricle; lane 10, right ventricle; lane 11, adult heart. The specific 177-bp stresscopin 1 cDNA bands are indicated by an arrowhead.
Figure 2C:
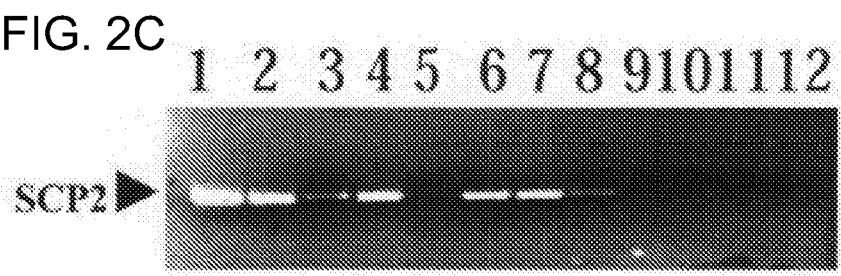
FIG. 2c. Expression of the stresscopin 2 transcript in 12 different human tissues of the digestive system as determined by PCR amplification using a primer pair flanking part of the ORF of stresscopin 2 cDNA and 1 ng of template cDNAs. Lane 1, ascending colon; lane 2, descending colon; lane 3, transverse colon; lane 4, duodenum; lane 5, Ileocecum; lane 6, Ileum; lane 7, jejunum; lane 8, stomach; lane 9, cecum; lane 10, rectum; lane 11, liver; lane 12, esophagus. The specific 237-bp stresscopin 2 cDNA bands are indicated by an arrowhead.
Figure 2D:
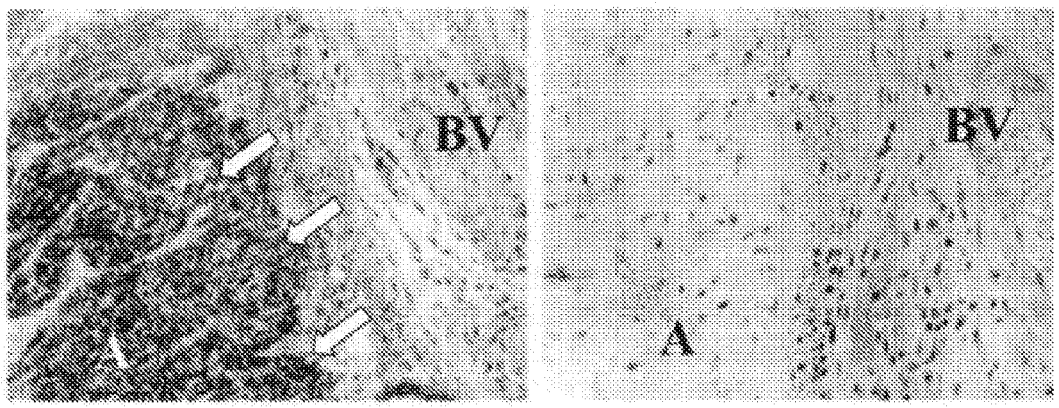
FIGS. 2d and 2e. Stresscopin 1 expression in mouse cardiac (d) and rat pituitary (e) sections using anti-stresscopin 1 antibody C2208. Specific signals (black particles) are indicated by arrows (left panel). Adjacent sections hybridized with anti-stresscopin 1 antibodies presaturated with the antigen peptide showed minimal staining (right panels). A, atrium tissues; BV, blood vessel; AP, anterior pituitary; PP, posterior pituitary; IL, intermediate lobe.
Figure 2E:
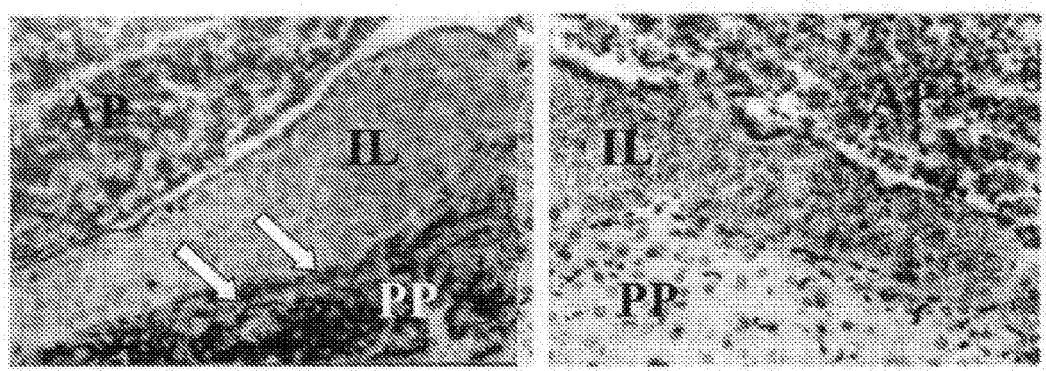
Figure 2F:
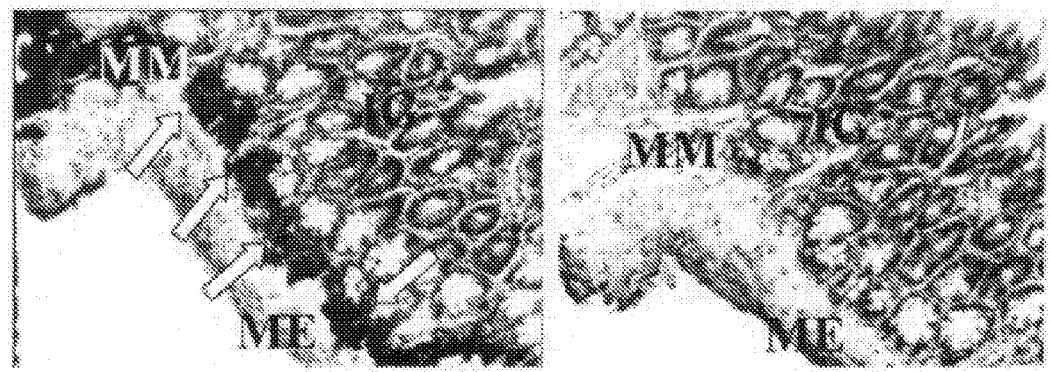
FIG. 2f, Stresscopin 2 expression in mouse intestinal sections using anti-stresscopin 2 antibody C2221 (left panel). A negative control with presaturated antibodies is shown on the right panel. MM, muscularis mucosae; IG, intestinal glands; ME, muscularis externa.

As shown in FIGS. 2b and 2c, the stresscopin 1 transcript could be amplified in various regions of human heart whereas the stresscopin 2 transcript was detected in the ascending colon, descending colon, transverse colon, duodenum, Ileum, jejunum, stomach, but not in Ileocecum, cecum, rectum, liver, and esophagus. In addition, immunohistochemical analysis using an anti-stresscopin 1 antibody detected specific stresscopin 1 signals in different regions of mouse heart with the atrium tissues showing a higher level of expression (FIG. 2d, left panel). In addition, immunoreactive stresscopin 1 was detected in the posterior pituitary (FIG. 2e, left panel). In contrast, specific staining for stresscopin 2 was detected in the muscularis mucosae of the small intestine using an anti-stresscopin 2 polyclonal antibody (FIG. 2f, left panel). Negative control staining using antibodies presaturated with free antigens showed no specific signals (FIGS. 2d, 2e, and 2f; right panels).

While stresscopin peptides could be the ligand for orphan GPCRs, the observation that ligand-receptor pairs usually co-evolved in diverse vertebrates suggests that the putative receptors for stresscopin peptides are likely related to the known CRH receptors and other group B GPCRs. Global sequence analysis based on all GPCR sequences in the GenBank using both pairwise sequence comparison and phylogenetic tree building indicated that the type-1 and type-2 CRH receptors are the most likely candidates to mediate the action of stresscopins because other closely related GPCRs are known to bind ligands with highly diverged structures (e.g. secretin and glucagon-related peptides) whereas no known orphan GPCR has an intermediate similarity. Two cell lines expressing CRHR1 (human retinoblastoma cell Y79) or CRHR2 (rat cardiac cell A7r5) were treated with the synthetic stresscopin 1 peptide. As shown in FIG. 3a, treatment with stresscopin 1 stimulated cAMP production by the cardiac cell line.

Surprisingly, this peptide was ineffective in Y79 cells (FIG. 3b), suggesting that stresscopin 1 activates only the type-2 CRH receptor. In contrast, both CRH and urocortin stimulated cAMP production in both cell lines. To expand this observation, 293T cells transiently transfected with different CRH receptor cDNAs were treated with synthetic stresscopin 1, stresscopin 2, or the pufferfish stresscopin peptide. Analysis of cAMP production showed that stresscopins are potent agonists for two isoforms of recombinant CRHR2, but not CRHR1 (FIGS. 3c-3e). Again, CRH and urocortin stimulated cAMP production mediated by all three receptors. While both human stresscopins and the pufferfish ortholog selectively activated type-2 CRH receptors, stresscopin 1 appeared to have a higher potency (>10-fold) as compared to stresscopin 2 and the pufferfish peptide.

Figure 3F:
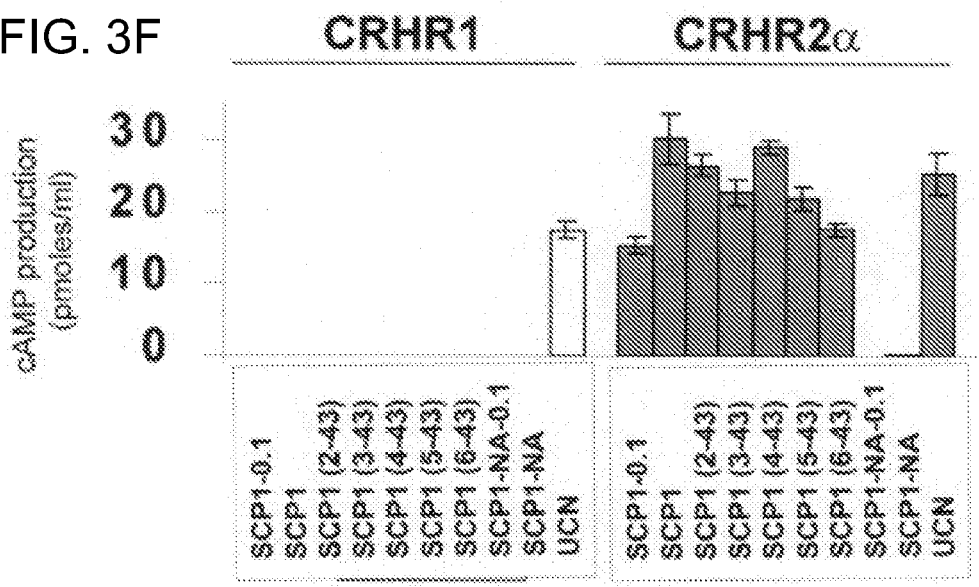
FIG. 3f. Full-length 43-amino-acid stresscopin 1 (SCP1) and truncated derivatives with deletion of 1-5 amino acids at the N-terminus (1 nM) stimulated cAMP production by recombinant CRH R2 (hatched bars), but not CRH R1 (blank bars). Nonamidated stresscopin 1 (SCP1-NA) showed a minimal stimulation of cAMP production as compared to the amidated counterpart. Data are the mean SEM (N=4). SCP1-0.1, stresscopin 1 (0.1 nM); SCP1, stresscopin 1 (1 nM); SCP1(2-43), truncated stresscopin 1 with the first amino acid deleted; SCP1(3-43), truncated stresscopin 1 with 2-amino-acid deletion; SCP1(4-43), truncated stresscopin 1 with 3-amino-acid deletion; SCP1(5-43), truncated stresscopin 1 with 4-amino-acid deletion; SCP1(6-43), truncated stresscopin 1 with 5-amino-acid deletion; SCP1-NA-0.1, full-length stresscopin 1 devoid of amidation at the C-terminus (0.1 nM); SCP1-NA, full-length stresscopin 1 devoid of amidation at the C-terminus (1 nM); UCN, urocortin.
Figure 3G:
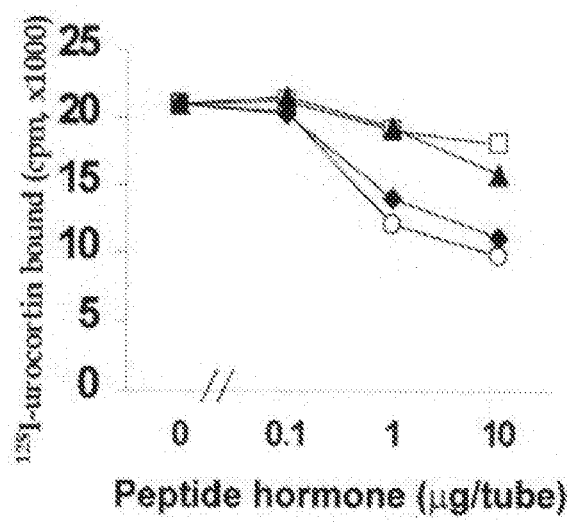
FIGS. 3g and 3h. Competitive displacement by unlabeled CRH, urocortin, stresscopin 1, and stresscopin 2 of $^{125}$I-labeled urocortin bound to membranes of 293T cells transfected with CRHR2 (FIG. 3g.) or CRHR2 (FIG. 3h.) cDNA. Data are mean SEM (N=3).
Figure 3H:
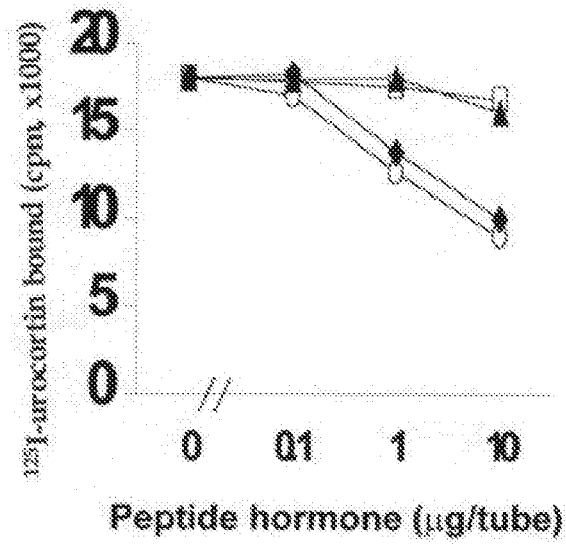

Because the proteolytic processing sites flanking the mature stresscopin 1 peptide do not correspond to those found in other CRH family peptides, 293T cells expressing CRHR1 or CRHR2 were treated with a panel of truncated stresscopin 1 peptides with deletions of 1 to 5 amino acids at the N-terminus and a nonamidated stresscopin 1 peptide to test the structural requirement for the selective activation of type-2 CRHR by stresscopin 1. As shown in FIG. 3f, full-length stresscopin 1 and truncated peptides all stimulated cAMP production by recombinant CRHR2, but not CRHR1. However, a stresscopin 1 peptide without amidation at the C-terminus showed a >50-fold reduction in its ability to stimulate cAMP production, suggesting that α-amidation is important for generating bioactive stresscopin 1. Furthermore, radioligand receptor binding assays using labeled urocortin confirmed the ability of stresscopin 1 and 2 peptides to bind CRHR2 and CRHR2 (FIGS. 3g and 3h).

Figure 4A:
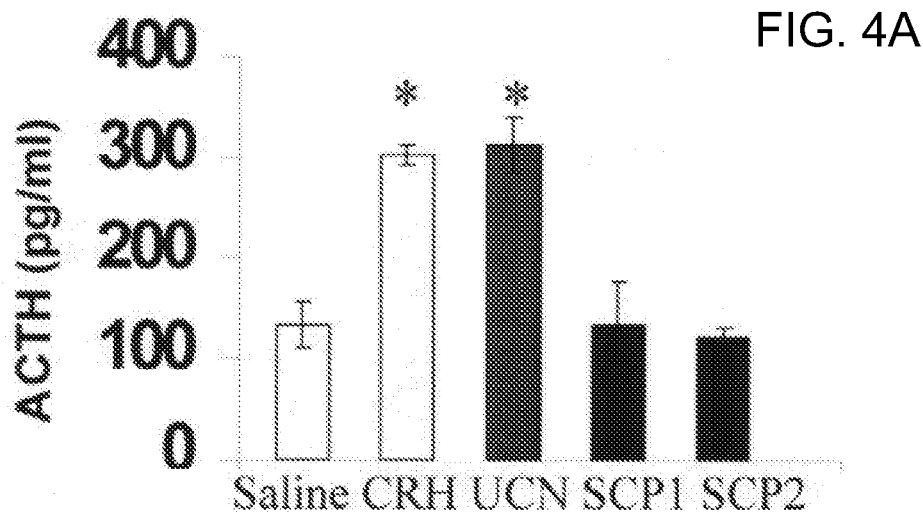
FIG. 4. CRH and urocortin, but not stresscopin 1 and stresscopin 2, stimulate ACTH release by cultured anterior pituitary cells in vitro (FIG. 4a) and induce ACTH secretion in vivo (FIG. 4b). ACTH contents in culture media and serum were determined using a radioimmunoassay. For in vivo studies, male rats were injected i.p. with test peptides (2 nmoles/kg B.W.) and sacrificed 30 min later. Data are mean SEM (N=4).
FIG. 4c. Anti-edema response regulated by stresscopins. Stresscopin 1 (20 nmoles/kg), stresscopin 2 (100 nmoles/kg), and related hormones (20 nmoles/kg) suppress heat-induced paw edema formation in anaesthetized rats (N=6).
FIG. 4d. Cumulative food intake in mice treated with stresscopin 1 (left panel, N=6) and stresscopin 2 (right panel, N=4) peptides and other hormones at 2, 4, and 8 h after treatment.
FIG. 4e. Reduction of gastric emptying by stresscopin 1 (blank bars, 8 nmoles/kg; hatched bars, 80 nmoles/kg), stresscopin 2 (blank bars, 80 nmoles/kg; hatched bars, 200 nmoles/kg), and related hormones (blank bars, 8 nmoles/kg; hatched bars, 80 nmoles/kg) at 2 h after hormone treatment (N=6). The rates of gastric emptying were calculated by the formula (wet weight of stomach at 2 h after treatment/wet weight of stomach in fed animals sacrificed at 0 h). SCP1 is stresscopin 1; SCP2 is stresscopin 2; UCN is urocortin; SCP1 (11-43) is truncated stresscopin 1 with the first 10 amino acids deleted.
Figure 4B:
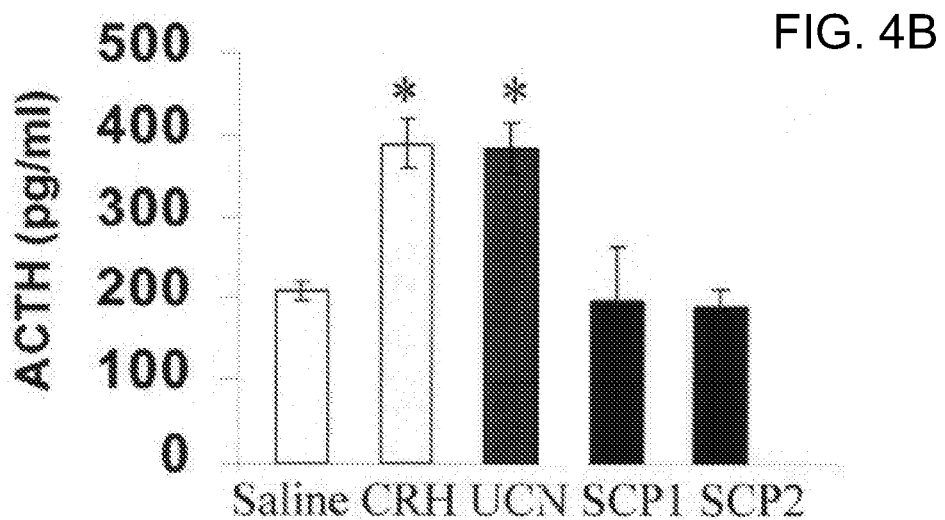
Figure 4C:
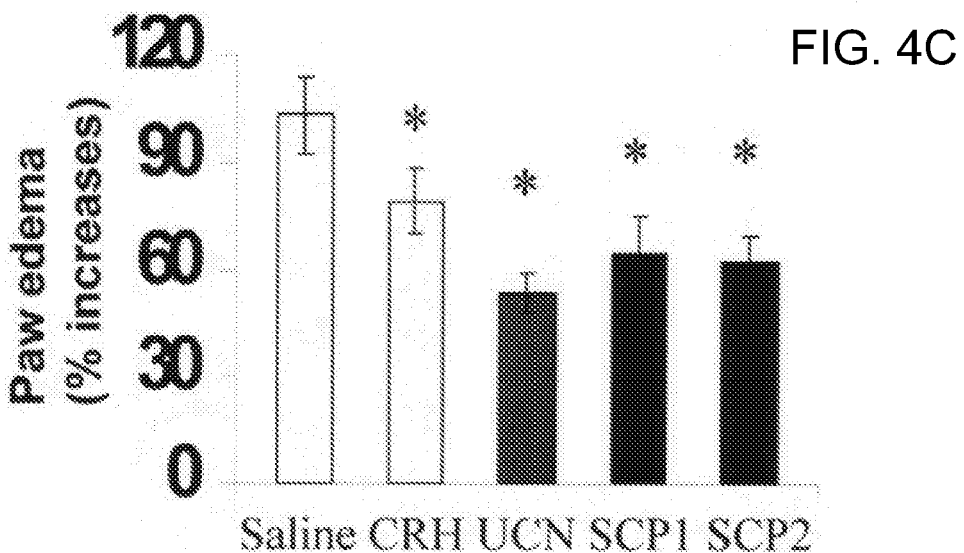

To confirm the specific activation of CRHR2 by stresscopin peptides, tests were conducted to determine the ability of human stresscopins and related hormones to stimulate ACTH secretion by cultured rat anterior pituitary cells, and to elicit ACTH release in intact male rats. As shown in FIGS. 4a and 4b, both in vitro and in vivo treatments with CRH and urocortin, but not stresscopin 1 or stresscopin 2, stimulated the release of ACTH, which is presumably mediated by CRH R1. Earlier studies indicated that CRH R2 mutant mice failed to show the enhanced cardiac performance or reduced blood pressure associated with systemic urocortin, but exhibited increased edema formation in response to thermal exposure. Based on the known association between urocortin-induced hypotension and anti-edema responses, the effects of stresscopins on heat-induced edema were tested to determine if edema is mediated by CRH R2. As shown in FIG. 4c, i.p. administration with stresscopin 1 or stresscopin 2 suppressed heat-induced edema formation in anesthetized rats, similar to that induced by urocortin and CRH. Because CRHR2 is essential for sustained feeding suppression induced by urocortin, the ability of stresscopins to regulate anorexic responses was also studied based on cumulative food intake in fasting mice.

Figure 4D:
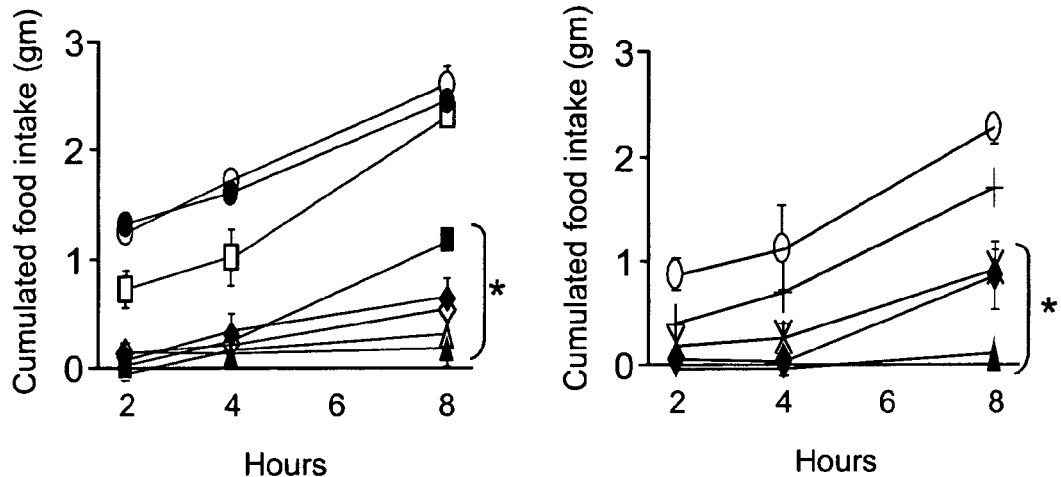
Figure 4E:
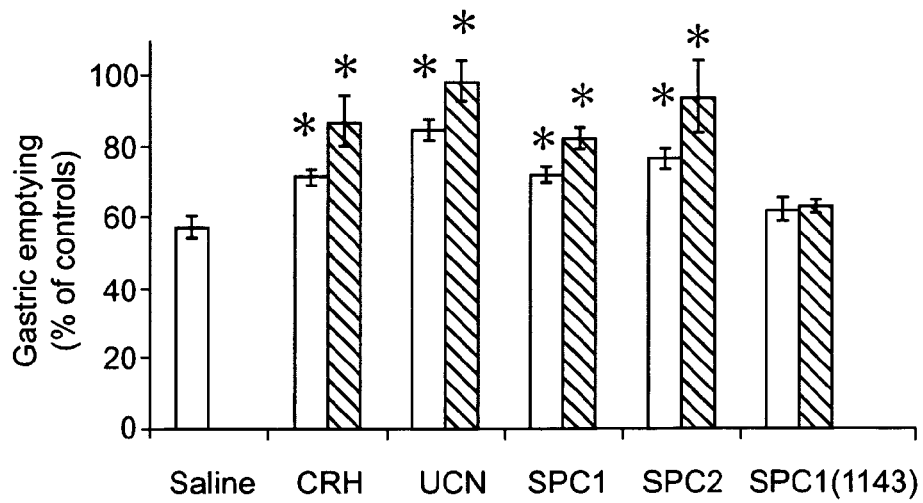

As shown in FIG. 4d, i.p. treatment with stresscopin 1 (left panel) or stresscopin 2 (right panel), like CRH and urocortin, dose-dependently decreased food intake in fasting mice. In contrast, a truncated stresscopin 1 peptide with a deletion of the first 10 amino acids at the N-terminus (SCP1(11-43)) has no effect on food intake in mice (left panel). Furthermore, stresscopin 1 and stresscopin 2 also suppressed gastric emptying activity as found for urocortin and CRH (FIG. 4e). This suggests that the anorexic effects of stresscopins are partly mediated at the level of the stomach.

As a result, these tests show stresscopin 1 and stresscopin 2 are novel selective and cogent ligands for CRHR2, and are likely important in the mediation of anorexic and vascular responses following stress. Unlike CRH and urocortin, stresscopins do not elicit ACTH release and the resultant elevations in glucocorticoids.

Initial stress-induced responses, such as gluconeogenesis and increases in arterial pressure and heart rate, provide a vital short-term metabolic lift, but prolonged or inappropriate exposure to stress can compromise homeostasis thereby leading to disease. Because CRHR2 is believed to be important in the regulation of the recovery phase of the stress response, the present findings suggest that stresscopin peptides represent important hormones in the protection of the organism to avoid damage incurred by prolonged and excessive exposure to the initial "flight or fight" response. This response is characterized by the activation of the CRH/ACTH/glucocorticoid axis and the release of catecholamines by the sympathetic adrenomedullary network. The stress-coping or "counter-shock" responses mediated by stresscopins in both central and peripheral tissues likely include the hypotensive, cardioprotective, anxiolytic, and anorexic responses mediated by CRH R2 expressed in brain, posterior pituitary, cardiac and skeletal muscle, spleen, and the gastrointestinal tract.

It is clear that adaptive responses induced by stressors are mediated by the autonomic nervous system and two interrelated and somewhat antagonistic CRH receptor pathways. Although the four mammalian CRH-related peptide hormones, CRH, urocortin, stresscopin 1, and stresscopin 2 show overlapping specificity to CRH R1 and CRH R2, optimal responses to stress depend on an integrated release of these endocrine/paracrine ligands in a tissue-specific and time-coordinated manner.

Table 1, shown below, describes the effects on body weight change and accumulative food intake in mice treated with stresscopin 1 or stresscopin 2. At 2 h after treatment, body weight and food intake were reduced in stresscopin-treated animals as compared to control mice receiving saline vehicle.

TABLE 1

Effects of Stresscopin 1 and Stresscopin 2 on food intake and body weight change in fasted animals.

| | Control | Stresscopin 1 (20 nM) | Stresscopin 2 (2 nM) | Stresscopin 2 (20 nM) |
|---|---|---|---|---|
| Average body weight change/mouse (grams, N = 5) | 0.98 ± 0.2 | 0.31 ± 0.14* | −0.19 ± 0.24* | 0.11 ± 0.1* |
| Average food intake/mouse (grams, N = 5) | 0.675 | 0.185 | 0.176 | 0.152 |

*Significantly different from control animals.

The experiments described herein should not be considered limiting on the invention, but merely illustrative to one skilled in the art, of the wide spectrum of possibilities for using stresscopin 1 and 2.

What is claimed is:

1. An isolated nucleic acid molecule comprising a nucleic acid sequence that encodes the polypeptide set forth in SEQ ID NO:6.

2. An isolated nucleic acid molecule comprising a nucleic acid sequence that encodes the polypeptide set forth in SEQ ID NO:5.

3. An isolated nucleic acid molecule comprising the nucleotide sequence set forth in SEQ ID NO:4.

4. The nucleic acid of claim 1, further comprising a vector sequence.

5. The nucleic acid of claim 4, wherein said vector comprises a transcription cassette operably linked to said nucleic acid sequence encoding the polypeptide of SEQ ID NO: 6.

6. The nucleic acid of claim 4, wherein said vector is a plasmid.

7. The nucleic acid of claim 4, wherein said vector sequence is a retroviral vector sequence.

8. The nucleic acid of claim 4, wherein said vector sequence is an adenoviral vector sequence.

* * * * *